United States Patent
Zatloukal et al.

(10) Patent No.: US 9,073,961 B2
(45) Date of Patent: Jul. 7, 2015

(54) SUBSTITUTION DERIVATIVES OF N$^6$-BENZYLADENOSINE-5'-MONOPHOSPHATE, METHODS OF PREPARATION THEREOF, USE THEREOF AS MEDICAMENTS, AND THERAPEUTIC PREPARATIONS CONTAINING THESE COMPOUNDS

(75) Inventors: Marek Zatloukal, Sumperk (CZ); Karel Dolezal, Hlubocky (CZ); Jiri Voller, Brno (CZ); Lukas Spichal, Olomouc (CZ); Miroslav Strnad, Olomouc (CZ)

(73) Assignees: UNIVERZITA PALACKEHO V OLOMOUCI, Olomouc (CZ); BIOAPEX, S.R.O., Olomouc (CZ)

( * ) Notice: Subject to any disclaimer, the term of this patent is extended or adjusted under 35 U.S.C. 154(b) by 331 days.

(21) Appl. No.: 13/642,905

(22) PCT Filed: Apr. 28, 2011

(86) PCT No.: PCT/CZ2011/000044
§ 371 (c)(1),
(2), (4) Date: Oct. 23, 2012

(87) PCT Pub. No.: WO2011/134444
PCT Pub. Date: Nov. 3, 2011

(65) Prior Publication Data
US 2013/0040908 A1 Feb. 14, 2013

(30) Foreign Application Priority Data
Apr. 29, 2010 (CZ) .................................... 2010-332

(51) Int. Cl.
*C07H 19/20* (2006.01)
*A61K 31/7068* (2006.01)
*C07H 19/167* (2006.01)

(52) U.S. Cl.
CPC .......... *C07H 19/167* (2013.01); *A61K 31/7068* (2013.01); *C07H 19/20* (2013.01)

(58) Field of Classification Search
CPC ...................................................... C07H 19/20
See application file for complete search history.

(56) References Cited

FOREIGN PATENT DOCUMENTS

WO    WO2004/058791    7/2004

OTHER PUBLICATIONS

Woenckhaus et al., "Preparations of Holodehydrogenases by Covalent Fixation of NAD+-Analogs to Alcohol and Lactate Dehydrogenase" Bioorganic Chemistry (1983) vol. 12 pp. 45-57.*
Dolezel et al., "Halogenation of N6-benzyladenosine decreases its cytotoxicity in human leukemia cells" Toxicology in vitro (2010) vol. 24 pp. 2079-2083.*
Eguchi et al., "Synthesis of AMP analogs and their use for studies on the allosteric site of rabbit muscle glycogen phosphorylase b" Journal of Biochemistry (1977) vol. 81 No. 5 pp. 1401-1411.*
Imahori, Kazutomo et al., "Purine nucleotides", Chemical Abstracts Service, Columbus, Ohio, XP002661696, May 12, 1984.
Ivanova, Mariyaua et al., "Endogenous cytokinins in shoots of Aloe polyphylla . . . ", Plant Growth Regulation, Kluwer Academic Publishers, Do, vol. 50, No. 2-3, Oct. 20, 2006.
Sakai, Keiko et al., "Affinity Labeling of the Allosteric Site of Fructose 1,6- Bis . . . ", Jrnl. of Biochem., Jap. Biochem. Soc., Oup, Tokyo, Japan, vol. 102, No. 2, Jan. 1, 1987.
Voller, J. et al., "Anticancer activity of natural cytokinins: A structure-activity relationship study", Phytochemistry, Pergamon Press, GB, vol. 71, No. 11-12, Aug. 1, 2010.

* cited by examiner

Primary Examiner — Eric Olson
(74) Attorney, Agent, or Firm — Notaro, Michalos & Zaccaria P.C.

(57) ABSTRACT

The invention relates to substitution derivatives of N$^6$-benzyladenosine-5'-monophosphate of the general formula I, wherein $(R)_n$ represents 1 to 4 substituents (n is in the range 1-4), which can be the same or different, and R is selected from the group comprising $C_1$ to $C_8$ alkyl, $C_1$ to $C_8$ alkoxy, amino, halogen, hydroxy, mercapto and nitro groups, and the pharmaceutically acceptable salts thereof. This invention also relates to methods of their preparation, their use as medicaments and in other biotechnological applications, and a therapeutic composition containing these derivatives.

18 Claims, 5 Drawing Sheets

I

SUBSTITUTION DERIVATIVES OF $N^6$-BENZYLADENOSINE-5'-MONOPHOSPHATE, METHODS OF PREPARATION THEREOF, USE THEREOF AS MEDICAMENTS, AND THERAPEUTIC PREPARATIONS CONTAINING THESE COMPOUNDS

FIELD OF ART

The invention relates to novel substitution derivatives of $N^6$-benzyladenosine-5'-monophosphate, having anticancer, antimitotic, and proapoptotic properties for animal cells, including human cells. This invention also relates to methods of their preparation and their use as drugs; therapeutic composition, which contains these derivatives as active compounds, and the use of these derivatives for the preparation of drugs and in pharmaceutical biotechnologies.

BACKGROUND ART

Cytokinins are important plant hormones that are defined by their ability to promote cell division in plant tissue culture in the presence of auxins (Skoog et al., Science 148, 532-533, 1965). Cytokinins so far found in plants are adenine derivatives substituted at the $N^6$-position with either an isoprenoid or an aromatic sidechain. Isoprenoid trans-zeatin (tZ) is the most abundant cytokinin. The abundance of other isoprenoid cytokinins—$N^6$-isopentenyladenine, iP, cis-zeatin, cZ and its derivative with a saturated sidechain dihydrozeatin (DHZ), varies between plant species. While isoprenoid cytokinins are ubiquitous in plants, aromatic cytokinins, represented by $N^6$-benzyladenine, BA, and its hydroxylated derivatives, the topolins) have only been identified, as yet, in a limited group of plant taxa (Horgan et al., Phytochemistry 14, 1005-1008, 1975; Strnad, Physiol. Plant. 101, 674-688, 1997; Strnad et al., Plant Physiol. 99, 74-80, 1992). The most abundant appears to be ortho-topolin riboside, which is present in micro-molar concentrations in poplar leaves after daybreak (Hewett et al., Planta 114, 119-129, 1973). Both families of cytokinins occur in several forms: free bases, ribosides, riboside-5'-monophosphates, 3-, 7-, 9- and O-glucosides, and amino acid conjugates.

Knowledge that cytokinins play key roles in the regulation of plant growth and differentiation led to the postulation that they have a potential utility for treating human diseases that involve dysfunctional cell proliferation and/or differentiation. The ability of cytokinin bases to induce or promote the differentiation of human cells has been demonstrated in keratinocytes (Berge et al., Ann. N. Y. Acad. Sci. 1067, 332-336, 2006) and several leukaemia cell lines, including HL-60 and K-562 (Ishii et al., Biochim. Biophys. Acta. 1643, 11-24, 2003). However, while free bases induce differentiation at relatively high concentrations (25-100 μM), their ribosides cause rapid apoptosis of leukemia cell lines in micromolar concentrations (Mlejnek, J. Cell Biochem. 83, 678-689, 2001). Cell death in HL-60 is preceded by depletion of adenosine triphosphate, activation of caspases and mitochondrial depolarization (Mlejnek, J. Cell Biochem. 83, 678-689, 2001; Ishii et al., Biochim. Biophys. Acta. 1643, 11-24, 2002). Intracellular conversion of ribosides into their monophosphates is necessary for their functioning (Meljnek and Doležel, Toxicol. In Vitro 19, 985-990, 2005). The caspase inhibition shifts the activity of $N^6$-isopentenyladenosine (iPR) in HL-60 to growth inhibitory and differentiating activity (Ishii et al., Biochim. Biophys. Acta. 1643, 11-24, 2002). It was recently shown that kinetin riboside (KR) could be a suitable drug candidate against multiple myeloma (Tiedemann et al., J. Clin. Invest. 118, 1750-1764, 2008). In several multiple myeloma models, KR induced rapid suppression of cyclin D1 and D2 transcription followed by cell-cycle arrest and tumour-specific apoptosis (Tiedemann et al., J. Clin. Invest. 118, 1750-1764, 2008). Cytotoxic effects of iPR, KR and $N^6$-benzyladenosine (BAR) against human cell lines derived from solid tumours were reported by Cabelo et al. (Int. J. Cancer 120, 2744-2748, 2008), Choi et al. (Cancer Lett. 261, 37-45, 2008), Laezza et al. (Int. J. Cancer. 124, 1322-1329, 2009), Meisel et al. (FEBS Lett. 433, 265-268, 1998) and Spinola et al. (Int. J. Cancer 120, 2744-2748, 2007). Depending on the cell line and cytokinin used, the treatment resulted in cell cycle block (either G1 or G2/M phase) and/or apoptosis. The in vivo anticancer activity of iPR, KR and BAR was also demonstrated in several animal and xenograft models of cancer (Choi et al., Cancer Lett. 261, 37-45, 2008; Laezza et al., FASEB J. 20, 412-418, 2006; Tiedemann et al., J. Clin. Invest. 118, 1750-1764, 2008). iPR and BAR also showed a promising activity against diverse malignancies in a small clinical trial (Mittelman et al., Ann. N. Y. Acad. Sci. 255, 225-234, 1975).

Micromolar concentrations of cytokinin ribosides and cytokinin bases are also able to induce cell death with features of apoptosis (activation of caspase-like proteases and fragmentation of DNA) in plant cell cultures (Mlejnek and Prochazka, Planta 215, 158-166, 2002). The cell death is also preceded by depletion of adenosine triphosphate and reactive oxygen species production. In contract to their hormonal activity which requires their interaction with a membrane receptor, the intracellular conversion of cytokinins into their monophosphates is necessary for their cytotoxic effect. The cytotoxic concentrations are higher than endogenous cytokinin levels in plant tissue but yet in the concentration range used in plant biotests (Carimi et al., Planta 216, 413-421, 2003; Mlejnek et al., Plant. Cell. Environ. 26, 1723-1735, 2003; Plant. Sci. 168, 389-395, 2005). Cytotoxic activity of naturally occuring cytokinins and their analogues (Doležal et al., Bioorg. Med. Chem. 14, 875-884, 2006; Bioorg. Med. Chem. 15, 3737-3747, 2007; CZ 294538) in mammalian and human experimental systems was demonstrated repeatedly.

It is an object of this invention to provide new anticancer and proapoptotic heterocyclic compounds derived from $N^6$-benzyladenosine-5'-monophosphate substituted on the phenyl moiety, having improved selectivity and therapeutic effectivity index, i.e., compounds which are less toxic but highly active. Hence they can be used for development of new generation of anticancer, antimitotic and proapoptotic drugs, as well as drugs with other medical activities.

DISCLOSURE OF THE INVENTION

Object of this invention are substitution derivatives of $N^6$-benzyladenosine-5'-monophosphate of the general formula I

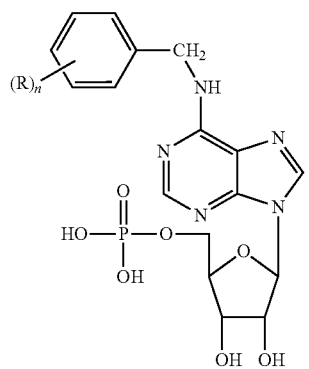

wherein (R)$_n$ represents 1 to 4 substituents R (n is within the range of 1-4), wherein R can be the same or different, and R is selected from the group comprising $C_1$ to $C_8$ alkyl, $C_1$ to $C_8$ alkoxy, amino, halogen, hydroxy, mercapto and nitro group, and pharmaceutically acceptable salts thereof.

The pharmaceutically acceptable salts of compounds of the general formula I comprise salts with alkali metals, ammonium or amines, or addition salts with acids. The pharmaceutically acceptable salts of compounds of the general formula I are selected preferably from the group comprising sodium and ammonium salts.

As used herein, the generic substituent groups have meanings defined in this legend, wherein: $C_1$ to $C_8$ alkyl denotes branched or unbranched alkyl chain containing 1 to 8 carbon atoms, preferably selected from the group comprising methyl, ethyl, propyl, isopropyl, butyl, isobutyl, pentyl, isopentyl, hexyl, and isohexyl, $C_1$ to $C_8$ alkoxy denotes the group —O—$R_a$, wherein $R_a$ is $C_1$ to $C_8$ alkyl or $C_3$ to $C_8$ cycloalkyl, amino denotes the group —$NH_2$, halogen is selected from the group comprising fluorine, bromine, chlorine and iodine atom, hydroxy denotes the group —OH, mercapto denotes the group —SH, nitro denotes the group —$NO_2$.

In the preferred embodiment, the derivatives of the general formula I comprise compounds wherein one of R is hydroxyl in the position 2 of the phenyl ring.

It is a further object of this invention to provide substitution derivatives of $N^6$-benzyladenosine-5'-monophosphate of the general formula I for use as medicaments.

It is an object of this invention to provide substitution derivatives of $N^6$-benzyladenosine-5'-monophosphate of the general formula I for use as inhibitors of protein kinases, preferably human kinase EPHB2.

It is another object of this invention to provide substitution derivatives of $N^6$-benzyladenosine-5'-monophosphate of the general formula I for use for inhibiting cell proliferation and/or inducing apoptosis.

It is a further object of this invention to provide substitution derivatives of $N^6$-benzyladenosine-5'-monophosphate of the general formula I for use as medicaments for the treatment of disorders which involve aberrant cell proliferation, such as cancer, leukemia, restenosis, rheumatoid arthritis, psoriasis, type I diabetes, multiple sclerosis, Alzheimer's disease, parasitoses caused by animals, funghi and/or protists, polycystic kidney disease, graft rejection (host versus graft disease), and gout.

Another object of the invention is also the use of the substitution derivatives of $N^6$-benzyladenosine-5'-monophosphate of the general formula I in the manufacture of a medicament for the treatment of disorders which involve aberrant cell proliferation, such as cancer, leukemia, restenosis, rheumatoid arthritis, lupus, type I diabetes, multiple sclerosis, Alzheimer's disease, parasitoses caused by animals, funghi and protists, polycystic kidney disease, graft rejection (host versus graft disease), and gout.

Inhibition by the compounds of the invention of the catalytic activity of protein kinases is mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated hyperactive form of the kinase and situations in which the kinase is present at excessive levels. Such compounds can also block excessive kinase activity in situations in which the further protein partner regulating the kinase is present at excessive levels or its binding to the kinase is enhanced. Furthermore, compounds which block kinase activity by interacting with the ATP binding site of the enzyme are also useful for inhibiting kinase activity in the situations in which a natural protein inhibitor of the kinase complexes is mutated.

Studies carried out on the derivatives of the invention have demonstrated, in addition, a strong effect on apoptosis of many cancer cell lines. It has been seen that apoptosis can be induced at stage $G_1$ or $G_2$ and following the damage of the DNA, some cells stop at stage $G_1$ and the p53-dependent apoptotic pathway is then induced. In other situations, it seems that cells stop at $G_2$/M stage in response to the damage caused to the DNA, and the activation of a p53-independent apoptotic path is observed. This path has proved particularly significant in the therapy of tumours in which lack of active p53 is observed. By the application of the derivatives of the invention, the p53-independent apoptosis will be stimulated in cells, which have stopped at stage $G_2$ through the damage to the DNA using agents such as mitoxantrone or cis-platinum. The inhibitors of this invention can thus increase the therapeutic potential of the anti-tumor agents currently used.

This invention also concerns substitution derivatives of $N^6$-benzyladenosine-5'-monophosphate of the general formula I, for use as medicaments for suppressing immunostimulation, e.g. arthritis, or in suppression of transplant rejection.

This invention also concerns substitution derivatives of $N^6$-benzyladenosine-5'-monophosphate of the general formula I, in the manufacture of a medicament for suppressing immunostimulation, e.g. in the treatment of arthritis or in suppression of transplant organ rejection.

A further object of this invention is the use of substitution derivatives of $N^6$-benzyladenosine-5'-monophosphate of the general formula I in tissue cultures for regulation of tissue proliferation and morphogenesis.

A further object of this invention is the use of compound of the general formula I in preparation of affinity absorption matrices, immobilised enzymes for process control, immunoassay reagents, diagnostic samples, as well as compounds and oligonucleotides labeled by $^{14}C$, $^3H$, avidin or biotin.

This invention also concerns the use of compound of the general formula I for in vitro cloning of plant and animal, preferably mammalian (except for the human), embryonic cells and embryos, preferably oocytes.

This invention further concerns the use of compounds of the general formula I as growth regulators of plants, microorganisms, yeast, fungi and animals, preferably mammals except for the human.

The following derivatives of formula I are particularly preferred, selected from the group comprising: 6-(2-fluorobenzylamino)purine riboside-5'-monophosphate, 6-(3-fluorobenzylamino)purine riboside-5'-monophosphate, 6-(4-fluorobenzylamino)purine riboside-5'-monophosphate, 6-(2-bromobenzylamino)purine riboside-5'-monophosphate, 6-(3-bromoobenzylamino)purine riboside-5'-monophosphate, 6-(4-bromobenzylamino)purine riboside-5'-monophosphate, 6-(2-iodobenzylamino)purine riboside-5'-monophosphate, 6-(3-iodobenzylamino)purinee riboside-5'-monophosphate, 6-(4-iodobenzylamino)purine riboside-5'-monophosphate, 6-(2-chlorobenzylamino)purine riboside-5'-monophosphate, 6-(3-chlorobenzylamino)purine riboside-5'-monophosphate, 6-(4-chlorobenzylamino)purine riboside-5'-monophosphate, 6-(2-nitrobenzylamino)purinee riboside-5'-monophosphate, 6-(3-nitrobenzylamino)purine riboside-5'-monophosphate, 6-(4-nitrobenzylamino)purine riboside-5'-monophosphate, 6-(5-nitro-2-methylbenzylamino)purine riboside-5'-monophosphate, 6-(2-methylbenzylamino)purine riboside-5'-monophosphate, 6-(3-methylbenzylamino)purine riboside-5'-monophosphate, 6-(4-methylbenzylamino)purine riboside-5'-monophosphate, 6-(2-methoxybenzylamino)purine riboside-5-monophosphate, 6-(3-methoxybenzylamino)purine riboside-5'-monophosphate, 6-(4-methoxybenzylamino)purine riboside-5'-monophosphate, 6-(2-hydroxybenzylamino)purine riboside-5'-monophosphate, 6-(3-hydroxybenzylamino)purine riboside-5'-monophosphate, 6-(4-hydroxybenzylamino)purine riboside-5'-monophosphate, 6-(2-ethoxybenzylamino)purine riboside-5'-monophosphate, 6-(3-ethoxybenzylamino)purine riboside-5'-monophosphate, 6-<4-ethoxybenzylamino)purine riboside-5'-monophosphate, 6-(4-ethylbenzylamino)purine riboside-5'-monophosphate, 6-(4-pentylbenzylamino)purine riboside-5'-monophosphate, 6-(4-pentyloxybenzylamino)purine riboside-5'-monophosphate, 6-(4-octylbenzylamino)purine riboside-5'-monophosphate, 6-(2,5-diaminobenzylamino)purine riboside-5'-monophosphate, 6-(3,5-dibromobenzylamino)purine riboside-5'-monophosphate, 6-(3,5-dibromo-4-methoxybenzylamino) purine riboside-5'-monophosphate, 6-(2,3-dichlorobenzylamino)purine riboside-5'-monophosphate, 6-(2,4-dichlorobenzylamino)purine riboside-5'-monophosphate. 6-(2,5-dichlorobenzylamino)purine riboside-5'-monophosphate, 6-(2,6-dichlorobenzylamino)purine riboside-5'-monophosphate, 6-(3,4-dichlorobenzylamino)purine riboside-5-monophosphate, 6-(3,5-dichlorobenzylamino) purine riboside-5-monophosphate. 6-(2,3,4,5-tetrafluorobenzylamino)purine riboside-5'-monophosphate, 6-(2-chloro-3,6-difluorobenzylamino)purine riboside-5'-monophosphate, 6-(5-chloro-2-fluorobenzylamino)purine riboside-5'-monophosphate, 6-(2,3,4-trifluorobenzylamino) purine riboside-5'-monophosphate, 6-(2,3,5-trifluorobenzylamino)purine riboside-5'-monophosphate, 6-(2,4,5-trifluorobenzylamino)purine riboside-5'-monophosphate, 6-(3,4,5-trifluorobenzylamino)purine riboside-5'-monophosphate, 6-(2,3,6-trifluorobenzylamino)purine riboside-5'-monophosphate, 6-(3-chloro-2,6-difluorobenzylamino)purine riboside-5'-monophosphate, 6-(2-chloro-6-fluorobenzylamino)purine riboside-5'-monophosphate, 6-(2,6-difluorobenzylamino)purine riboside-5'-monophosphate, 6-(2,4-difluorobenzylamino)purine riboside-5-monophosphate. 6-(3,4-difluorobenzylamino)purine riboside-5'-monophosphate, 6-(2,5-difluorobenzylamino)purine riboside-5'-monophosphate, 6-(3,5-difluorobenzylamino)purine riboside-5'-monophosphate, 6-(2-chloro-6-fluoro-3-methylbenzylamino)purine purine riboside-5'-monophosphate, 6-(6-chloro-2-fluoro-3-methylbenzylamino)purine riboside-5'-monophosphate, 6-(2,3-difluoro-4-methylbenzylamino)purine riboside-5'-monophosphate, 6-(2,6-difluoro-3-methylbenzylamino)purine riboside-5'-monophosphate, 6-(3-chloro-2,6-difluorobenzylamino)purine riboside-5'-monophosphate, 6-(3-fluoro-4-methyl benzylamino)purine riboside-5'-monophosphate, 6-(4-fluoro-3-methylbenzylamino)purine riboside-5'-monophosphate, 6-(5-fluoro-2-methylbenzylamino)purine riboside-5'-monophosphate, 6-(2-chloro-3,6-difluorobenzylamino)purine riboside-5'-monophosphate, 6-(2-chloro-4-fluorobenzylamino)purine riboside-5'-monophosphate, 6-(3,4-dihydroxybenzylamino)purine riboside-5'-monophosphate, 6-(3,5-dihydroxybenzylamino)purine riboside-5'-monophosphate, 6-(3,4-dihydroxybenzylamino) purine riboside-5'-monophosphate, 6-(2,4-dihydroxybenzylamino) purine riboside-5'-monophosphate, 6-(2,5-dihydroxybenzylamino)purine riboside-5'-monophosphate, 6-(2,6-dihydroxybenzylamino)purine riboside-5'-monophosphate, 6-(3,4-dimethoxybenzylamino)purine riboside-5'-monophosphate, 6-(3,5-dimethoxybenzylamino) purine riboside-5'-monophosphate, 6-(2,3-dimethoxybenzylamino)purine riboside-5'-monophosphate, 6-(2,4-dimethoxybenzylamino)purine riboside-5'-monophosphate, 6-(2,5-dimethoxybenzylamino)purine riboside-5'-monophosphate, 6-(2,6-dimethoxybenzylamino)purine ribo side-5'-monophosphate, 6-(2-hydroxy-3-methoxybenzylamino) purine riboside-5'-monophosphate, 6-(2-hydroxy-4-methoxybenzylamino)purine riboside-5'-monophosphate, 6-(2-hydroxy-5-methoxybenzylamino)purine riboside-5'-monophosphate, 6-(2-hydroxy-6-methoxybenzylamino)purine ribo side-5'-monophosphate, 6-(3-hydroxy-2-methoxybenzylamino)purine riboside-5'-monophosphate, 6-(3-hydroxy-4-methoxybenzylamino)purine riboside-5'-monophosphate, 6-(3-hydroxy-5-methoxybenzylamino) purine riboside-5'-monophosphate, 6-(3-hydroxy-6-methoxybenzylamino)purine riboside-5'-monophosphate, 6-(4-hydroxy-2-methoxybenzylamino)purine riboside-5'-monophosphate, 6-(4-hydroxy-3-methoxybenzylamino)purine riboside-5'-monophosphate, 6-(4-hydroxy-5-methoxybenzylamino)purine riboside-5'-monophosphate, 6-(4-hydroxy-6-methoxybenzylamino)purine riboside-5'-monophosphate, 6-(2-hydroxy-3,4-dimethoxybenzylamino) purine riboside-5'-monophosphate, 6-(2-hydroxy-3,5-dimethoxybenzylamino)purine riboside-5'-monophosphate, 6-(2-hydroxy-3,6-dimethoxybenzylamino)purine riboside-5'-monophosphate, 6-(2-hydroxy-4,5-dimethoxybenzylamino)purine riboside-5'-monophosphate, 6-(2-hydroxy-4,6-dimethoxybenzylamino)purine riboside-5'-monophosphate, 6-(2-hydroxy-5,6-dimethoxybenzylamino) purine riboside-5'-monophosphate, 6-(3-hydroxy-4,5-dimethoxybenzylamino)purine riboside-5'-monophosphate, 6-(3-hydroxy-4,6-dimethoxybenzylamino)purine riboside-5'-monophosphate, 6-(3-hydroxy-2,4-dimethoxybenzylamino)purine riboside-5'-monophosphate, 6-(3-hydroxy-2,5-dimethoxybenzylamino)purine riboside-5'-monophosphate, 6-(3-hydroxy-2,6-dimethoxybenzylamino) purine riboside-5'-monophosphate, 6-(4-hydroxy-2,3-dimethoxybenzylamino)purine riboside-5'-monophosphate, 6-(4-hydroxy-2,5-dimethoxybenzylamino)purine riboside-5'-monophosphate, 6-(4-hydroxy-2,6-dimethoxybenzylamino)purine riboside-5'-monophosphate, 6-(4-hydroxy-3,5-dimethoxybenzylamino)purine riboside-5'-monophosphate, 6-(4-hydroxy-3,6-dimethoxybenzylamino) purine ribo side-5'-monophosphate, 6-(2,3-dihydroxy-4-methoxybenzylamino)purine riboside-5'-monophosphate, 6-(2,3-dihydroxy-5-methoxybenzylamino)purine riboside-5'-monophosphate, 6-(2,3-dihydroxy-6-methoxybenzylamino)purine riboside-5'-monophosphate, 6-(2,4-dihydroxy-3-methoxybenzylamino)purine riboside-5'-monophosphate, 6-(2,4-dihydroxy-5-methoxybenzylamino)purine riboside-5'-monophosphate, 6-(2,4-dihydroxy-6-methoxybenzylamino)purine riboside-5'-monophosphate, 6-(2,5-dihydroxy-3-methoxybenzylamino)purine riboside-5'-monophosphate, 6-(2,5-dihydroxy-4-methoxybenzylamino)purine riboside-5'-monophosphate, 6-(2,5-dihydroxy-6-methoxybenzylamino)purine riboside-5'-monophosphate, 6-(2,6-dihydroxy-3-methoxybenzylamino) purine riboside-5'-monophosphate, 6-(2,6-dihydroxy-4-methoxybenzylamino)purine riboside-5'-monophosphate, 6-(2,6-dihydroxy-5-methoxybenzylamino)purine riboside- 5'-monophosphate, 6-(3,4-dihydroxy-2-methoxybenzylamino)purine riboside-5'-monophosphate, 6-(3,4-dihydroxy-5-methoxybenzylamino)purine riboside-5'-monophosphate, 6-(3,4-dihydroxy-6-methoxybenzylamino)purine riboside-5'-monophosphate, 6-(3,5-dihydroxy-2-methoxybenzylamino)purine riboside-5'-monophosphate, 6-(3,5-dihydroxy-4-methoxybenzylamino)purine riboside-5'-monophosphate, 6-(3,5-dihydroxy-6-methoxybenzylamino)purine ribo side-5'-monophosphate, 6-(2,3,4-trimethoxybenzylamino)purine riboside-5'-monophosphate, 6-(2,4,5-trimethoxybenzylamino)purine riboside-5'-monophosphate, 6-(2,4,6-trimethoxybenzylamino)purine riboside-5'-monophosphate, 6-(3,4,5-trimethoxybenzylamino)purine riboside-5'-monophosphate, 6-(2-hydroxy-3,4,5-trimethoxybenzylamino)purine riboside-5'-monophosphate, 6-(2-hydroxy-3,4,6-trimethoxybenzylamino)purine riboside-5'-monophosphate, 6-(2-hydroxy-4,5,6-trimethoxybenzylamino)purine riboside-5'-monophosphate, 6-(2,4,6-trimethoxybenzylamino)purine riboside-5'-monophosphate, 6-(2,3,4-trihydroxybenzylamino)purine riboside-5'-monophosphate, 6-(2,4,6-trihydroxybenzylamino)purine riboside-5'-monophosphate, 6-(2,3,4-trihydroxybenzylamino)purine ribo side-5'-monophosphate, 6-(3,4,5-trihydroxybenzylamino)purine riboside-5'-monophosphate, 6-(2,4,6-trihydroxybenzylamino)purine ribo side-5'-monophosphate, 6-(2-hydroxy-3-chlorobenzylamino)purine ribo side-5'-monophosphate, 6-(2-hydroxy-4-chlorobenzylamino)purine riboside-5'-monophosphate, 6-(2-hydroxy-5-chlorobenzylamino)purine riboside-5'-monophosphate, 6-(2-hydroxy-6-chlorobenzylamino)purine riboside-5'-monophosphate, 6-(2-hydroxy-3-iodobenzylamino)purine ribo side-5'-monophosphate, 6-(2-hydroxy-4-iodobenzylamino)purine ribo side-5'-monophosphate, 6-(2-hydroxy-5-iodobenzylamino)purine ribo side-5'-monophosphate, 6-(2-hydroxy-6-iodobenzylamino)purine ribo side-5'-monophosphate, 6-(2-hydroxy-3-bromobenzylamino)purine ribo side-5'-monophosphate, 6-(2-hydroxy-4-bromobenzylamino)purine ribo side-5'-monophosphate, 6-(2-hydroxy-5-bromobenzylamino)purine ribo side-5'-monophosphate, 6-(2-hydroxy-6-bromobenzylamino)purine ribo side-5'-monophosphate, 6-(2-hydroxy-3-fluorobenzylamino)purine riboside-5'-monophosphate, 6-(2-hydroxy-4-fluorobenzylamino)purine riboside-5'-monophosphate, 6-(2-hydroxy-5-fluorobenzylamino)purine riboside-5'-monophosphate, 6-(2-hydroxy-6-fluorobenzylamino)purine riboside-5'-monophosphate, 6-(2-hydroxy-3-methylbenzylamino)purine ribo side-5'-monophosphate, 6-(2-hydroxy-4-methylbenzylamino)purine riboside-5'-monophosphate, 6-(2-hydroxy-5-methylbenzylamino)purine riboside-5'-monophosphate, 6-(2-hydroxy-6-methylbenzylamino)purine ribo side-5'-monophosphate, 6-(2,3-dihydroxy-4-chloroobenzylamino)purine riboside-5'-monophosphate, 6-(2,3-dihydroxy-5-chlorobenzylamino)purine ribo side-5'-monophosphate, 6-(2,5-dihydroxy-4-chlorobenzylamino)purine ribo side-5'-monophosphate, 6-(2,6-dihydroxy-4-chlorobenzylamino)purine ribo side-5'-monophosphate, 6-(2,6-dihydroxy-4-iodobenzylamino)purine ribo side-5'-monophosphate, 6-(2,6-dihydroxy-3-chlorobenzylamino)purine riboside-5'-monophosphate, 6-(2,6-dihydroxy-3-bromobenzylamino)purine riboside-5'-monophosphate, 6-(2,6-dihydroxy-3-iodobenzylamino)purine riboside-5'-monophosphate, 6-(2,6-dihydroxy-3-fluoroobenzylamino)purine riboside-5'-monophosphate, 6-(2,6-dihydroxy-3,5-dichlorobenzylamino)purine riboside-5'-monophosphate, 6-(2,6-dihydroxy-3,5-dibromobenzylamino)purine riboside-5'-monophosphate, 6-(2,6-dihydroxy-3,5-diiodobenzylamino)purine riboside-5'-monophosphate, 6-(2,6-dihydroxy-3,5-difluorobenzylamino)purine riboside-5'-monophosphate, 6-(4,5-dimethoxy-2-nitrobenzylamino)purine riboside-5'-monophosphate, 6-(3,4-dimethylbenzylamino)purine riboside-5'-monophosphate, 6-(2,3-dimethylbenzylamino)purine riboside-5'-monophosphate, 6-(2,4-dimethylbenzylamino)purine riboside-5'-monophosphate, 6-(2,6-dimethylbenzylamino)purine riboside-5'-monophosphate, 6-(2,6-dimethyl-4-hydroxybenzylamino)purine riboside-5'-monophosphate, 6-(3,5-dimethyl-4-hydroxybenzylamino)purine riboside-5'-monophosphate, 6-(2-fluoro-4-hydroxybenzylamino)purine riboside-5'-monophosphate, 6-(3-fluoro-4-methylbenzylamino)purine riboside-5'-monophosphate, 6-(3,4-dinitrobenzylamino)purine riboside-5'-monophosphate, 6-(3,5-dinitrobenzylamino)purine riboside-5'-monophosphate, 6-(2-methyl-5-nitrobenzylamino)purine riboside-5'-monophosphate, 6-(3-methyl-4-nitrobenzylamino)purine riboside-5'-monophosphate, 6-(3,4-diiodo-4-hydroxybenzylamino)purine riboside-5'-monophosphate, 6-(2-chloro-3,4-dimethoxybenzylamino)purine riboside-5'-monophosphate, 6-(4-chloro-3,5-dinitrobenzylamino)purine riboside-5'-monophosphate, 6-(2-chloro-4-fluorobenzylamino)purine riboside-5'-monophosphate, 6-(3-chloro-4-fluorobenzylamino)purine riboside-5'-monophosphate, 6-(2-chloro-6-methylbenzylamino)purine riboside-5'-monophosphate, 6-(3-chloro-2-methylbenzylamino)purine riboside-5'-monophosphate, 6-(3-chloro-4-methylbenzylamino)purine riboside-5'-monophosphate, 6-(5-chloro-2-methoxybenzylamino)purine riboside-5'-monophosphate, 6-(2-chloro-4-fluorobenzylamino)purine riboside-5'-monophosphate, 6-(2-chloro-5-nitrobenzylamino)purine riboside-5'-monophosphate, 6-(2-chloro-6-nitrobenzylamino)purine riboside-5'-monophosphate, 6-(4-chloro-3-nitrobenzylamino)purine riboside-5'-monophosphate, 6-(5-chloro-2-nitrobenzylamino)purine riboside-5'-monophosphate, 6-(3-bromo-4-hydroxybenzylamino)purine riboside-5'-monophosphate, 6-(3,5-dibromo-4-hydroxybenzylamino)purine, 6-(3-bromo-4-methoxybenzylamino)purine, 6-(4-butoxybenzylamino)purine riboside-5'-monophosphate, 6-(4-/t-butyl/benzylamino)purine riboside-5'-monophosphate, 6-(4-t-butyl-2,6-dimethylbenzylamino)purine riboside-5'-monophosphate, 6-(2-aminobenzylamino)purine riboside-5'-monophosphate, 6-(3-aminobenzylamino)purine riboside-5'-monophosphate, 6-(4-aminobenzylamino)purine riboside-5'-monophosphate, 6-(2-amino-3-chlorobenzylamino)purine riboside-5'-monophosphate, 6-(2-amino-4-chlorobenzylamino)purine riboside-5'-monophosphate, 6-(2-amino-5-chlorobenzylamino)purine riboside-5'-monophosphate, 6-(2-amino-6-chlorobenzylamino)purine riboside-5'-monophosphate, 6-(3-amino-2-chlorobenzylamino)purine riboside-5'-monophosphate, 6-(3-amino-4-chlorobenzylamino)purine riboside-5'-monophosphate, 6-(3-amino-5-chlorobenzylamino)purine riboside-5'-monophosphate, 6-(3-amino-6-chlorobenzylamino)purine riboside-5'-monophosphate, 6-(2,6-diamino-3-chlorobenzylamino)purine riboside-5'-monophosphate, 6-(2,6-diamino-4-chlorobenzylamino)purine riboside-5'-monophosphate, 6-(4-amino-3-chlorobenzylamino)purine riboside-5'-monophosphate, 6-(4-amino-5-dichlorobenzylamino)purine riboside-5'-monophosphate, 6-(5-amino-2-methylbenzylamino)purinee riboside-5'-monophosphate, 6-(2-amino-3-nitrobenzylamino)purinee riboside-5'-monophosphate, 6-(4-amino-3-nitrobenzylamino)purine riboside-5'-monophosphate, 6-(2,4,5-trichlorobenzylamino)purine riboside-5'-monophosphate, 6-(2,4,5-trichlorobenzylamino)purine riboside-5'-monophosphate, 6-(2,4,6-trichlorobenzylamino)purine riboside-5'-monophosphate, 6-(2,3,4-trichlorobenzylamino)purine riboside-5'-monophosphate, 6-(2,3,5-trichlorobenzylamino)purine riboside-5'-monophosphate, 6-(2,3,6-trichlorobenzylamino)purine riboside-5'-monophosphate, 6-(2,5,6-trichlorobenzylamino)purine riboside-5'-monophosphate.

The starting material for the preparation of the compounds of the general formula I is 6-chloropurine riboside-5'-monophosphate. Another starting material for the preparation of the compounds of the general formula I is 6-bromopurine riboside-5'-monophosphate; both starting materials are known from literature or commercially available. Another starting material for the preparation of the compounds of the general formula I is 6-fluoropurine riboside-5'-monophosphate, which can be prepared from 6-chloropurine riboside-5'-monophosphate by reaction with triethylamine under the formation of quaternary ammonium salt, which can be converted by reaction with tetrabutylammonium triphenydifluorosilicate in dimethylformamid to 6-fluoropurine riboside-5'-monophosphate (Gurvich et al., Nucleos. Nucleot. 18: 2327 (1999)).

Yet another starting material for the preparation of the compounds of the general formula I are substituted benzylamines. Those having one or more hydroxyl groups, are not commercially available and may be prepared by demethylation of appropriate methoxyderivatives using 48% HBr in $N_2$ atmosphere.

This invention also concerns preparation of substitution derivatives of $N^6$-benzyladenosine-5'-monophosphate of the general formula I, wherein R and n have the above mentioned meanings, and wherein 6-halogenopurine riboside-5'-monophosphate, wherein halogen is selected from the group containing bromine, chlorine or fluorine, is subjected to a nucleophilic substitution with benzylamine substituted by one to four R substitutents, which can be the same or different, wherein R has the above mentioned meaning.

Therapeutic Compositions

The therapeutic composition comprises about 1% to about 95% of the active ingredient, single-dose forms of administration preferably comprising about 20% to about 90% of the active ingredient and administration forms, which are not single-dose preferably comprising about 5% to about 20% of the active ingredient. Unit dose forms may be, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, if possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine.

Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length $C_8$ to $C_{12}$ from Hills AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example into ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and, if appropriate, stabilizers. The active ingredient can also be present here in the form of a lyophilisate, if appropriate, together with excipients, and be dissolved before parenteral administration by addition of suitable solvents. Solutions such as are used, for example, for parental administration can also be used as infusion solutions. Preferred preservatives are, for example, antioxidants, such as ascorbic acid, or microbicides, such as sorbic or benzoic acid.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The compounds can be administered prophylactically or therapeutically as such or in the form of pharmaceutical compositions, preferably in an amount which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
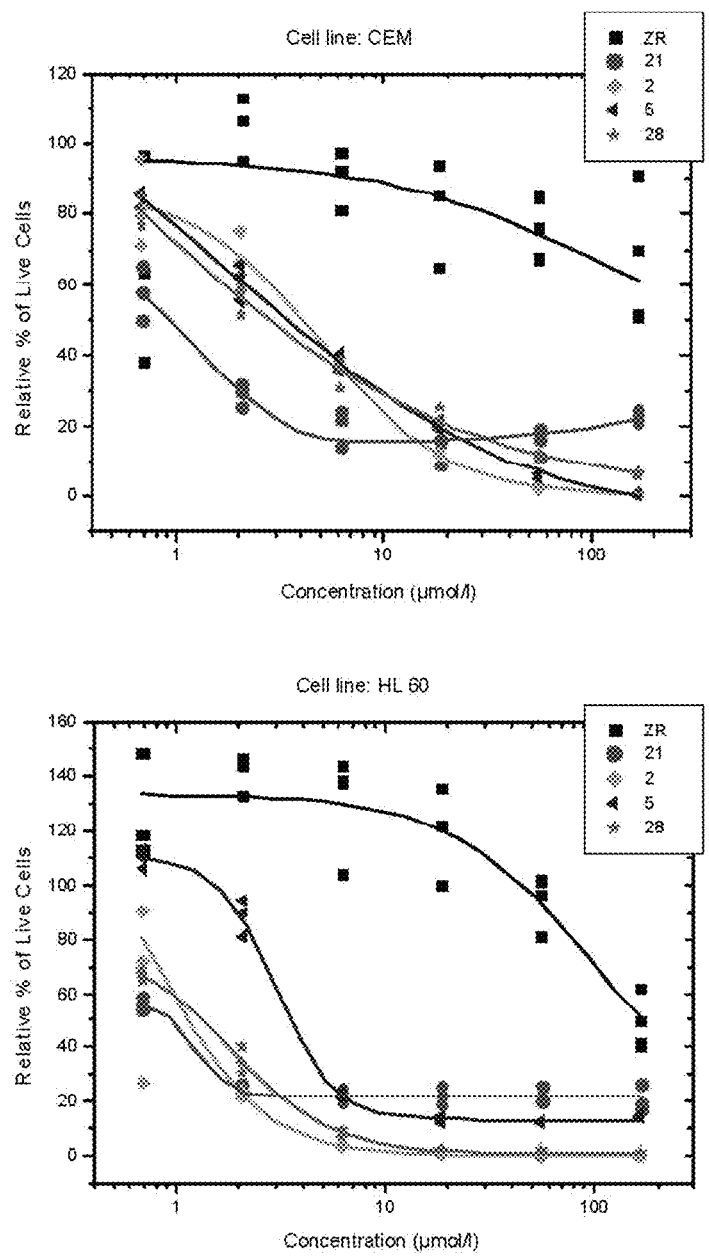
FIG. 1. shows the inhibition of growth of cancer cell lines CEM and HL60 by the compounds of the general formula I. The cytotoxicity was measured using Calcein AM assay. The activity is presented as percentage of maximum activity (in the absence of inhibitor). The dose-dependent antiproliferative activity. ZR: zeatin riboside-5'-monophosphate; compound 21: ortho-topolin riboside-5'-monophosphate (=6-(2-hydroxybenzylamino)purine riboside-5'-monophosphate); 2: 6-(3-fluorobenzylamino)purine riboside-5'-monophosphate; 5: 6-(3-chlorobenzylamino)purine riboside-5'-monophosphate; 28: 6-(2-hydroxy-3-methoxybenzylamino)purine riboside-5'-monophosphate.

The following examples serve to illustrate the invention and should not be construed as limiting the scope thereof.

The starting material for the compounds of the formula I is available from commercial sources (Sigma-Aldrich, Fluka, Olchemim, etc.). Melting points were determined on a Koffler block and are uncorrected. Evaporations were carried out on a rotary evaporator under vacuum at temperatures below 80° C. The $^1$H NMR spectra (σ, ppm; J, Hz) were measured on Varian VXR-400 (400 MHz) or on Varian Unity 300 (300 MHz) instruments. All spectra were obtained at 25° C. using tetramethylsilane as an internal standard. Electron impact mass spectra m/z (rel.%, composition, deviation) were measured on a VG 7070E spectrometer (70 eV, 200° C., direct inlet). Quadrupole mass spectra were measured on a Micromass ZMD detector with electrospray ionization. Merck silica gel Kieselgel 60 (230-400 mesh) was used for column chromatography. All compounds gave satisfactory elemental analyses (±0.4%).

Example 1

Preparation of Compounds of the General Formula I

Compounds were prepared from 6-chloropurine-9β-D-riboside-5'-O-monophosphate, disodium salt dihydrate, by nucleophilic substitution with the corresponding substituted benzylamine in the presence of N,N-diisopropyl-N-ethylamine in methanol. The reaction was carried out at 90° C. for a period of 12 hours at atmospheric pressure. The solvent was removed by vacuum evaporation and the raw product was further purified by RP C18 flash chromatography (mobile phase 15% methanol in water) followed by crystallization from 2-propanol. Purity of the final product was 95% (HPLC) and the yield 60-70%.

TABLE 1

Compounds Prepared by the Method of Example 1
(listed compounds are anhydrous disodium salts)

| No. | Substituent at the position 6 of purine | Elemental analyses calculated/found % C | % H | % N | ES-MS [M − H⁻] |
|---|---|---|---|---|---|
| 1 | 2-fluorobenzylamino | 40.9/40.8 | 3.4/3.4 | 14.0/13.9 | 454 |
| 2 | 3-fluorobenzylamino | 40.9/50.0 | 3.4/3.4 | 14.0/14.1 | 454 |
| 3 | 4-fluorobenzylamino | 40.9/40.9 | 3.4/3.3 | 14.0/14.0 | 454 |
| 4 | 2-chlorobenzylamino | 39.6/39.8 | 3.3/3.2 | 13.6/13.5 | 470 |
| 5 | 3-chlorobenzylamino | 39.6/39.8 | 3.3/3.3 | 13.6/13.4 | 470 |
| 6 | 4-chlorobenzylamino | 39.6/39.6 | 3.3/3.2 | 13.6/13.7 | 470 |
| 7 | 2-bromobenzylamino | 36.4/36.5 | 3.1/3.0 | 12.5/12.3 | 515 |
| 8 | 3-bromobenzylamino | 36.4/36.2 | 3.1/3.2 | 12.5/12.3 | 515 |
| 9 | 4-bromobenzylamino | 36.4/36.5 | 3.1/3.1 | 12.5/12.6 | 515 |
| 10 | 2-iodobenzylamino | 33.6/33.4 | 2.8/2.7 | 11.5/11.4 | 562 |
| 11 | 3-iodobenzylamino | 33.6/33.5 | 2.8/2.8 | 11.5/11.3 | 562 |
| 12 | 2-methylbenzylamino | 43.6/43.7 | 4.1/4.1 | 14.1/14.0 | 450 |
| 13 | 3-methylbenzylamino | 43.6/43.4 | 4.1/4.0 | 14.1/13.8 | 450 |
| 14 | 4-methylbenzylamino | 43.6/43.8 | 4.1/4.2 | 14.1/14.0 | 450 |
| 15 | 2-methoxybenzylamino | 42.3/42.3 | 3.9/3.8 | 13.7/13.7 | 466 |
| 16 | 3-methoxybenzylamino | 42.3/42.2 | 3.9/3.9 | 13.7/13.5 | 466 |
| 17 | 4-methoxybenzylamino | 42.3/42.2 | 3.9/3.8 | 13.7/13.8 | 466 |
| 18 | 2-aminobenzylamino | 41.1/41.0 | 3.9/3.9 | 16.9/16.7 | 451 |
| 19 | 3-aminobenzylamino | 41.1/41.2 | 3.9/4.0 | 16.9/16.7 | 451 |
| 20 | 4-aminobenzylamino | 41.1/41.1 | 3.9/3.9 | 16.9/17.1 | 451 |
| 21 | 2-hydroxybenzylamino | 41.1/41.0 | 3.9/3.9 | 16.9/16.7 | 451 |
| 22 | 3-hydroxybenzylamino | 41.1/41.2 | 3.9/4.0 | 16.9/16.7 | 451 |
| 23 | 4-hydroxybenzylamino | 41.1/41.1 | 3.9/3.9 | 16.9/17.1 | 451 |
| 24 | 2,4-dichlorobenzylamino | 37.1/37.0 | 2.9/2.8 | 12.7/12.7 | 504 |
| 25 | 3,4-dichlorobenzylamino | 37.1/37.2 | 2.9/2.9 | 12.7/12.5 | 504 |
| 26 | 2,3-dihydroxybenzylamino | 39.8/39.9 | 3.5/3.5 | 13.6/13.5 | 468 |
| 27 | 3,5-dihydroxybenzylamino | 39.8/39.8 | 3.5/3.4 | 13.6/13.3 | 468 |
| 28 | 2-hydroxy-3-methoxybenzylamino | 41.0/41.2 | 3.8/3.8 | 13.3/13.3 | 482 |
| 29 | 2-hydroxy-5-methoxybenzylamino | 41.0/41.1 | 3.8/3.7 | 13.3/13.2 | 482 |
| 30 | 3-hydroxy-4-methoxybenzylamino | 41.0/41.0 | 3.8/3.9 | 13.3/13.1 | 482 |
| 31 | 2,3-dimethoxybenzylamino | 42.1/42.0 | 4.1/4.0 | 12.9/12.8 | 496 |
| 32 | 2,4-dimethoxybenzylamino | 42.1/42.1 | 4.1/4.0 | 12.9/12.9 | 496 |
| 33 | 3,4-dimethoxybenzylamino | 42.1/42.0 | 4.1/4.1 | 12.9/12.7 | 496 |
| 34 | 3,5-dimethoxybenzylamino | 42.1/42.1 | 4.1/4.0 | 12.9/12.8 | 496 |
| 35 | 4-hydroxy-3,5-dimethoxybenzylamino | 40.9/40.8 | 4.0/4.1 | 12.6/12.4 | 512 |
| 36 | 2,4-difluorobenzylamino | 39.5/39.8 | 3.1/3.2 | 13.5/13.2 | 472 |
| 37 | 3,5-difluorobenzylamino | 39.5/39.4 | 3.1/3.1 | 13.5/13.3 | 472 |
| 38 | 2,3,4-trifluorobenzylamino | 38.1/38.3 | 2.8/2.8 | 13.1/12.9 | 490 |
| 39 | 2,4,5-trifluorobenzylamino | 38.1/38.2 | 2.8/2.7 | 13.1/13.0 | 490 |
| 40 | 2,3,6-trifluorobenzylamino | 38.1/38.1 | 2.8/2.8 | 13.1/12.8 | 490 |
| 41 | 3-chloro-4-fluorobenzylamino | 38.3/38.4 | 3.0/3.0 | 13.1/12.9 | 488 |
| 42 | 2-hydroxy-3-methylbenzylamino | 42.3/42.3 | 3.9/3.8 | 13.7/13.5 | 466 |
| 43 | 2-hydroxy-3-fluorobenzylamino | 39.6/39.4 | 3.3/3.3 | 13.6/13.5 | 470 |
| 44 | 2-hydroxy-3-iodobenzylamino | 32.8/32.7 | 2.7/2.7 | 11.2/11.1 | 578 |
| 45 | 2-hydroxy-5-methoxybenzylamino | 41.0/41.0 | 3.8/3.8 | 13.3/13.0 | 482 |
| 46 | 2-hydroxy-5-methylbenzylamino | 42.3/42.4 | 3.9/3.9 | 13.7/13.9 | 466 |
| 47 | 2-hydroxy-5-chlorobenzylamino | 38.4/38.5 | 3.2/3.2 | 13.2/13.0 | 486 |
| 48 | 2-hydroxy-5-fluorobenzylamino | 39.6/39.4 | 3.3/3.3 | 13.6/13.5 | 470 |
| 49 | 2-amino-5-fluorobenzylamino | 39.7/39.7 | 3.5/3.4 | 16.3/16.0 | 469 |

Example 2

3 mmol of 6-fluoropurine riboside-5'-monophosphate was dissolved in 15 ml n-propanol. Subsequently, 3.15 mmol of 2,3-dihydroxybenzylamine hydrobromide and 10 mmol of triethylamine was added. The reaction was carried out at 90 ºC for a period of 6 hours. After cooling, the precipitated product was filtered off, washed with cold (5° C.) n-propanol (2×5 ml) and was further purified by RP C18 flash chromatography, mobile phase 15-20% methanol, followed by crystallization from ethanol. TLC: chloroform-methanol-ammonia (90:9:0.1). Yield 65-70%.

TABLE 2

Compounds Prepared by the Method of Example 2
(listed compounds are anhydrous disodium salts)

| No | Substituent at the position 6 of purine | Elemental analyses calculated/found % C | % H | % N | ES-MS [M − H⁻] |
|---|---|---|---|---|---|
| 26 | 2,3-dihydroxybenzylamino | 39.8/39.6 | 3.5/3.5 | 13.6/13.5 | 468 |
| 27 | 3,5-dihydroxybenzylamino | 39.8/39.8 | 3.5/3.5 | 13.6/13.4 | 468 |
| 28 | 2-hydroxy-3-methoxybenzylamino | 41.0/41.2 | 3.8/3.8 | 13.3/13.3 | 482 |

TABLE 2-continued

Compounds Prepared by the Method of Example 2
(listed compounds are anhydrous disodium salts)

| No | Substituent at the position 6 of purine | Elemental analyses calculated/found | | | ES-MS [M − H⁻] |
|----|----|----|----|----|----|
| | | % C | % H | % N | |
| 30 | 3-hydroxy-4-methoxybenzylamino | 41.0/41.0 | 3.8/3.9 | 13.3/13.1 | 482 |
| 31 | 2,3-dimethoxybenzylamino | 42.1/42.0 | 4.1/4.0 | 12.9/12.8 | 496 |
| 32 | 2,4-dimethoxybenzylamino | 42.1/42.1 | 4.1/4.0 | 12.9/12.9 | 496 |
| 33 | 3,4-dimethoxybenzylamino | 42.1/42.0 | 4.1/4.1 | 12.9/12.7 | 496 |
| 34 | 3,5-dimethoxybenzylamino | 42.1/42.1 | 4.1/4.0 | 12.9/12.8 | 496 |
| 35 | 4-hydroxy-3,5-dimethoxybenzylamino | 40.9/40.8 | 4.0/4.1 | 12.6/12.4 | 512 |

Example 3

In Vitro Cytotoxic Activity of Novel Derivatives

Because toxic compounds negatively influence metabolic processes in cells, many standard cytotoxicity assays are based on measurement of metabolisation rate of various artificial substrates. Resulting product is then quantified e.g. by means of spectrometry. The assays can be easily modified for use in 96-well plates. For evaluation of cytotoxic effect of the novel substituted 9-substituted cytokinin derivatives of this invention, a microtiter assay based on quantification of metabolisation of Calcein AM was used. The assay is widely used in drug screening programs and in chemosensitivity testing. In the living cells, Calcein AM is enzymatically hydrolysed and accumulation of resulting calcein is manifested by green fluorescence.

In the routine screening the following cell lines have been used: CEM (T-lymphoblastoid leukemia), HL-60 (promyelocytic leukemia), K-562 (human erythroleukemia), MCF-7 (breast carcinoma), HOS (human osteogenic sarcoma), and G-361 (human malignant melanoma). Normal human fibroblasts BJ were used as a control for routine screening of the compounds. The cells were kept in Nunc/Corning 80 cm² plastic bottles and grown in cell culture medium (DMEM containing 5 g/l glucose, 2 mM glutamine, 100 U/ml penicilline, 100 µg/ml streptomycine, 10% fetal bovine serum and sodium hydrogencarbonate), the compounds were prepared according to the procedure of the present invention.

The cell suspensions were prepared and diluted according to the particular cell type and the expected target cell density (2.500-30.000 cells per well based on cell growth characteristics) and pippetted (80 µl) into 96-well plates. Inoculates were allowed a pre-incubation period of 24 hours at 37° C. and 5% $CO_2$ for stabilisation. Tested compound was added in total volume of 20 µl of water at time zero. Usually, test compound was evaluated at six 3-fold dilutions. In routine testing, the highest concentration tested was 166.7 µM. All drug concentrations were tested in triplicates. Incubations of cells with the test compounds lasted for 72 hours at 37° C., in 5% $CO_2$ atmosphere and 100% humidity. At the end of incubation period Calcein AM in PBS was added into final concentration of 1 µg/ml. After another 1 hour of incubation fluorescence (FD) was measured with the Labsystem FIA Reader Fluoroscan Ascent (Microsystems). Tumor cell survival (TCS) was estimated using the following equation: GI50=($FD_{drug\ exposed\ well}$/$FD_{control\ well}$)×100%. The GI50 value, the drug concentration causing 50% reduction of esterase activity, was calculated from the obtained dose response curves (FIG. 1).

Cytotoxicity of novel compounds was tested on panel of cell lines of different histogenetic and species origin (Table 3). We show here that equal activities were found in all tumour cell lines tested, however, the non-malignant cells, e.g. BJ fibroblasts and normal human lymphocytes, were resistant to new compounds induced cytotoxicity. The effective novel derivatives killed tumour cells in concentrations close to 0.1-50 µM.

TABLE 3

Cytotoxicity of Substitution Derivatives of adenosine for Different Cancer Cell Lines

| | Cell line tested/GI50 (µmol/L) | | | | | | |
|---|---|---|---|---|---|---|---|
| | HOS | K-562 | MCF7 | BJ | G-361 | CEM | HL60 |
| adenosine | >166.7 | >166.7 | >166.7 | >166.7 | >166.7 | >166.7 | >166.7 |
| zeatin riboside | >166.7 | >166.7 | >166.7 | >166.7 | >166.7 | >166.7 | >166.7 |
| Substituent at N⁶-position of the purine ring | | | | | | | |
| 2-hydroxybenzylamino | 2.5 | 4 | 10.5 | 43.2 | 13.5 | 1.3 | 0.48 |
| 3-hydroxybenzylamino | >166.7 | >166.7 | >166.7 | >166.7 | >166.7 | 51.9 | 23.7 |
| 4-hydroxybenzylamino | >166.7 | >166.7 | >166.7 | >166.7 | >166.7 | 39.7 | 9.5 |
| 2-methoxybenzylamino | 21.2 | 11.2 | >166.7 | >166.7 | >166.7 | 3.2 | 2.3 |
| 3-methoxybenzylamino | >166.7 | >166.7 | >166.7 | >166.7 | >166.7 | 7.6 | 4.9 |
| 2-chlorobenzylamino | >166.7 | 64 | >166.7 | >166.7 | | 14.5 | 1.6 |
| 3-chlorobenzylamino | >166.7 | 30.4 | >166.7 | >166.7 | | 1.6 | 0.75 |
| 4-chlorobenzylamino | >166.7 | 16.1 | >166.7 | >166.7 | | 6.5 | 5.3 |
| 2-fluorobenzylamino | >166.7 | 33.2 | >166.7 | | | 4.6 | 3.2 |
| 3-fluorobenzylamino | >166.7 | 7 | 16.6 | >166.7 | 15.7 | 4 | 0.92 |
| 4-fluorobenzylamino | 20 | 6.4 | 14 | >166.7 | | 1.5 | 0.86 |
| 2-methylbenzylamino | >166.7 | >166.7 | >166.7 | >166.7 | | 14 | 3.3 |
| 3-methylbenzylamino | >166.7 | >166.7 | >166.7 | >166.7 | | 19.1 | 6.4 |
| 2-bromobenzylamino | >166.7 | 10 | >166.7 | >166.7 | | 12.3 | 6.6 |
| 3-bromobenzylamino | >166.7 | 19.7 | >166.7 | >166.7 | | 5 | 8 |

TABLE 3-continued

Cytotoxicity of Substitution Derivatives of adenosine for Different Cancer Cell Lines

| | Cell line tested/GI50 (µmol/L) | | | | | | |
|---|---|---|---|---|---|---|---|
| | HOS | K-562 | MCF7 | BJ | G-361 | CEM | HL60 |
| 4-bromobenzylamino | >166.7 | 68.2 | >166.7 | >166.7 | | 20.6 | 47.7 |
| 2,4-dimethoxybenzylamino | >166.7 | >166.7 | >166.7 | >166.7 | | >166.7 | 39 |
| 2-chloro-4-fluorobenzylamino | >166.7 | 11.7 | >166.7 | >166.7 | | 20.9 | 9 |
| 3-chloro-4-fluorobenzylamino | >166.7 | 4.1 | >166.7 | >166.7 | | 3.4 | 3.5 |
| 2,3-dimethoxybenzylamino | >166.7 | >166.7 | >166.7 | >166.7 | | >166.7 | 109 |
| 2,4-dichlorobenzylamino | >166.7 | 85.7 | 126.9 | >166.7 | | 86.7 | 96.3 |
| 2,4-difluorobenzylamino | >166.7 | 7.4 | >166.7 | >166.7 | | 7.1 | 3.4 |
| 2,3,4-trifluorobenzylamino | >166.7 | >166.7 | >166.7 | >166.7 | | 58.2 | 13 |
| 3,4-dichlorobenzylamino | >166.7 | 6.5 | 88.8 | >166.7 | | 3 | 1.1 |
| 3,5-difluorobenzylamino | >166.7 | >166.7 | >166.7 | >166.7 | | 24.5 | 9.1 |
| 3,5-dimethoxybenzylamino | >166.7 | >166.7 | >166.7 | >166.7 | | | 18.8 |
| 2,3,6-trifluorobenzylamino | >166.7 | >166.7 | >166.7 | >166.7 | | | 13 |
| 2-hydroxy-3-methoxybenzylamino | 24.1 | 2.1 | 30.4 | 69.7 | 27.9 | 0.3 | 0.5 |
| 3-hydroxy-4-methoxybenzylamino | >166.7 | >166.7 | >166.7 | >166.7 | | 79.3 | 68.9 |
| 2-hydroxy-5-methoxybenzylamino | 6.4 | 15.4 | 21 | 87.9 | 12.3 | 0.9 | 0.54 |
| 2-hydroxy-5-chlorobenzylamino | 10.6 | 15.7 | 18 | 63.4 | 12.5 | 0.6 | 0.47 |
| 2-hydroxy-5-fluorobenzylamino | 9.1 | 13.4 | 16 | 58.7 | 10.7 | 0.5 | 0.53 |

Example 4

Induction of Cancer Cell Apoptosis

To analyse the mechanisms of induced cytotoxicity by the novel compounds, it is important to distinguish apoptosis from the other major form of cell death, necrosis. First, at tissue level, apoptosis produces little or no inflammation, since the resulting cell fragments are engulfed by neighbouring cells, especially by macrophages, rather than being released into the extracellular fluid. In contrast, in necrosis, cellular content is released into the extracellular fluid, and thus has an irritant effect on the nearby cells, causing inflammation. Second, at the cellular level, apoptotic cells exhibit shrinkage and blebbing of the cytoplasm, preservation of structure of cellular organelles including the mitochondria, condensation and margination of chromatin, fragmentation of nuclei, and formation of apoptotic bodies, thought not all of these are seen in all cell types. Third, at the molecular level, a number of biochemical processes take an important role in induction of apoptosis. However, majority of them is not well understood, and they result in activation of proteases and nucleases, which finally destruct key biological macromolecules—proteins and DNA.

Effect of Novel Compounds on Activity of Caspases-3

In the course of apoptosis, caspase cascade is activated. Caspase-3 is an effector caspase that plays a role in the induction of some changes typical for apoptosis (chromatin condensation, DNA fragmentation).

Leukemia cell line CEM was cultured in cell culture medium (DMEM containing 5 g/l glucose, 2 mM glutamine, 100 U/ml peniciline, 100 µg/ml streptomycine, 10% fetal calf serum and sodium bicarbonate). 24 hours before treatment, cell suspensions were centrifuged, diluted to concentration of 500000 cells per ml with fresh medium and pipetted in 50 L aliquotes into 96-well plate. After 12 and 24 hours of incubation with the test compound, the activity of caspase-3 was measured using commercial kit (Apo-ONE, Promega) that is based on quantification of hydrolysis of fluorogenic substrate Z-DEVD-R110 (excitation 480 nm/emission 520 nm). Reaction specifity was confirmed in a control experiment, when both test compound and caspase-3 inhibitor Ac-DEVD-CHO were added. All experiments were done in triplicate.

Figure 2:
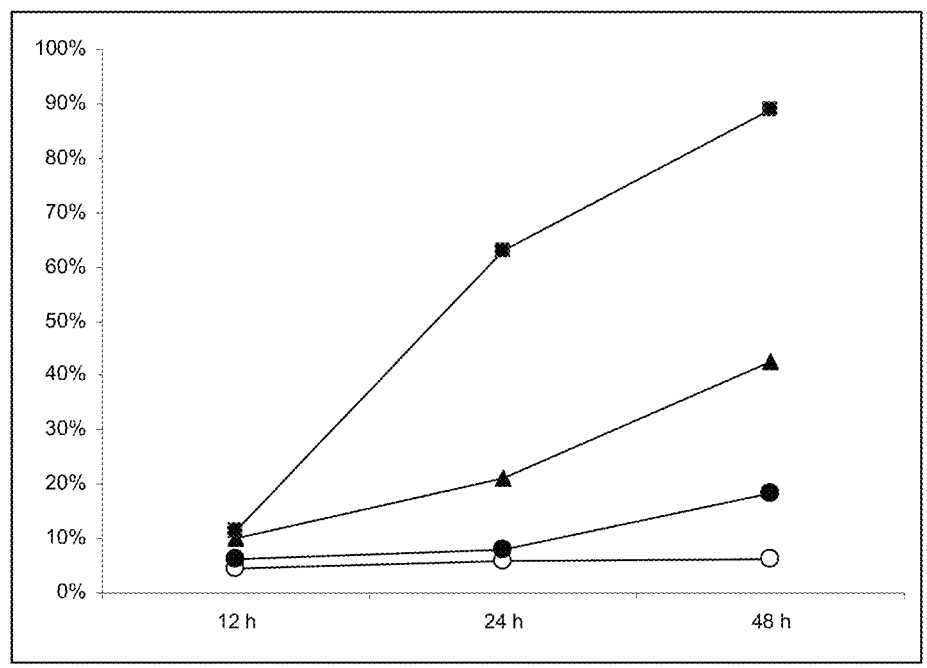
FIG. 2 shows the effect of compound 21 on DNA fragmentation. y-axis is the percentage of apoptotic sub-G1 fraction. Cancer cell linie CEM was incubated with compound 21 in concentrations corresponding to IC50 (1.3 µM,•), triple IC50 (▲) and fivefold IC50 (■). Control cells (○) were cultivated with DMSO vehiculum.

FIG. 2 shows that ortho-topolin riboside-5'-monophosphate (compound 21) activates caspase-3 and that level of the activation is time dependent.

Example 5

Analysis of Apoptosis Using Flow Cytometry (DNA Fragmentation Induction)

One of the hallmarks of apoptosis is fragmentation of DNA. It can be measured by flowcytometry of the cells stained with propidium iodide. Because the fragmentation results in a loss of a fraction of the nuclear DNA, apoptotic cells have a lower DNA content than cells in G1 phase of cell cycle and can be detected as a subG1 peak in the histogram.

Leukemia cell line CEM was cultured in cell culture medium (DMEM containing 5 g/l glucose, 2 mM glutamine, 100 U/ml penicillin, 100 µg/ml streptomycine, 10% fetal calf serum and sodium bicarbonate). 24 hours before treatment, cell suspensions were centrifuged, diluted with fresh medium to concentration of 100000 cells per ml with fresh medium and pipetted in 10 ml aliquotes Petri dishes. After an incubation for a given time period, the cells were collected by centrifugation (4° C., 600 g), washed with PBS (4° C.) and fixed with 70% ethanol at −20° C. overnight. Low molecular weight DNA fragmentse were extracted with citrate buffer (11.36 g trisodium citrate dihydrate/l). The nuclei were stained with the solution of propidium iodide in PBS (10 µg/ml) containing RNase A (60 IU per sample). After 1 hour incubation the samples were analyzed by flowcytometry (excitation 488 nm, emission above 620 nm).

Figure 3:
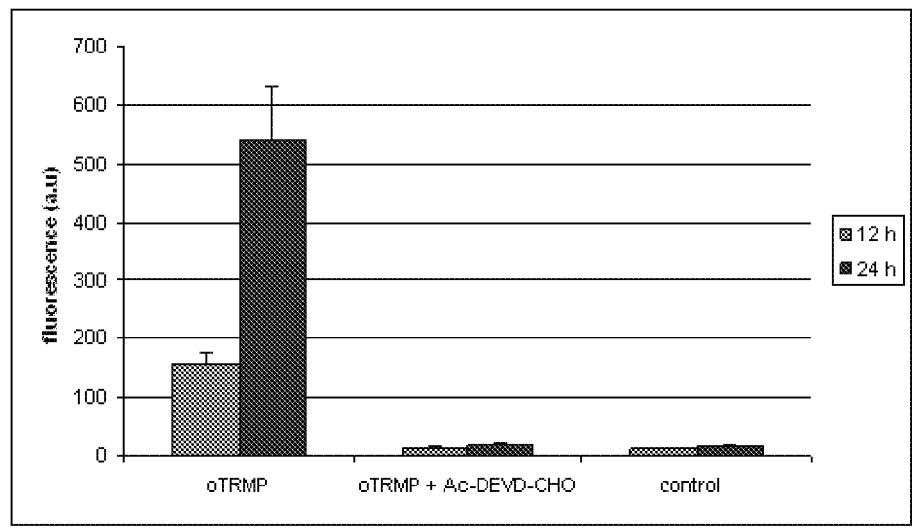
FIG. 3 displays induction of activity of caspase-3 by compound 21 (10 µM).

FIG. 3 shows that in leukemia cell line CEM induction of DNA fragmentation is dependent on the concentration of compound 21 and the time of the treatment. The effect was visible already after 12 hours.

Example 6

Detection of Apoptosis on the Basis of Cell Morphology

Cell Culture.

A suspension of human promyelocytic HL-60 cells was cultured in RPMI-1640 medium supplemented with a 10% calf foetal serum and antibiotics in 5% $CO_2$ atmosphere at 37° C. Cell number was determined using hematocytometr. HL-60 cells were obtained from ECACC.
Cell Viability Assay.

Double staining with fluorescein diacetate (FDA, 2 □g/ml) and propidium iodide (PI, 10 µg/ml) directly in growth medium. The percentage of dead cells (i.e., red stained cells) was evaluated using fluorescence microscopy (Mlejnek and Kolman 1999, Chem. Biol. Interact. 1999, 117: 219-239).
Morphological Analysis of Cell Nuclei.

Figure 4:
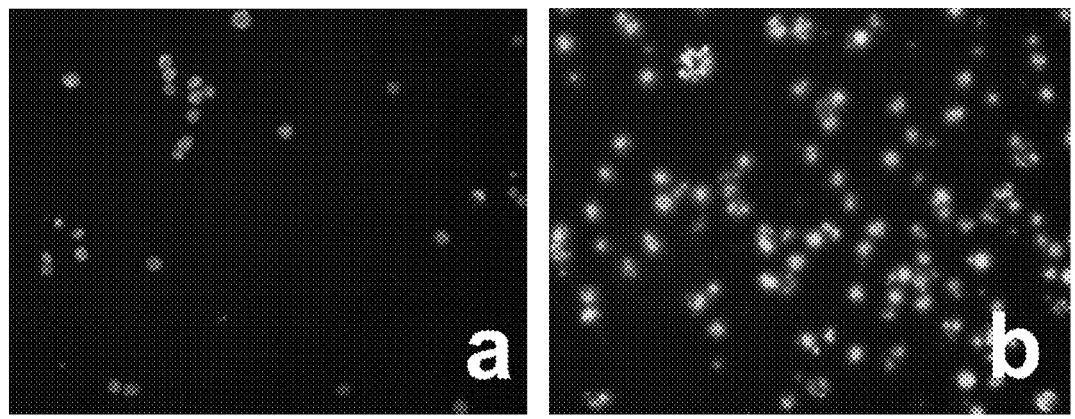
FIG. 4 shows the effect of compound 21 on HL-60 cell nuclear morphology. a) Nuclei of cells cultivated at standard conditions in medium without compound 21; b) nuclei of cells cultivated in medium containing 5 µM of compound 21 for 24 hours.

Cells were harvested, washed in PBS, and fixed in methanol/acetic acid (3:1) fixation mixture at −20° C. for 12 hours. Aliquots of cells were spread on glass slides and stained with Hoechst 33342 (2 µg/ml) in PBS/glycerol (v/v, 70:30). The morphology of cell nuclei was examined by a fluorescence microscope Olympus BX60 (Mlejnek and Kuglik, J. Cell. Biochem. 2000, 77:6-17). The demonstration of apoptotic cells by this method is shown in FIG. 4.

Example 7

Figure 5:
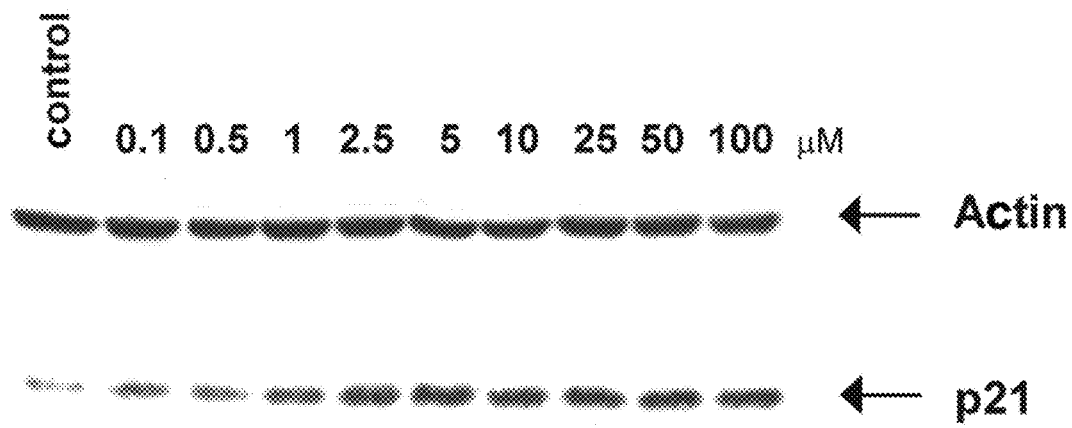
FIG. 5 shows induction of protein $p21^{WAF-1}$ in MCF-7 cells after treatment with different concentrations of compound 28.
Figure 6:
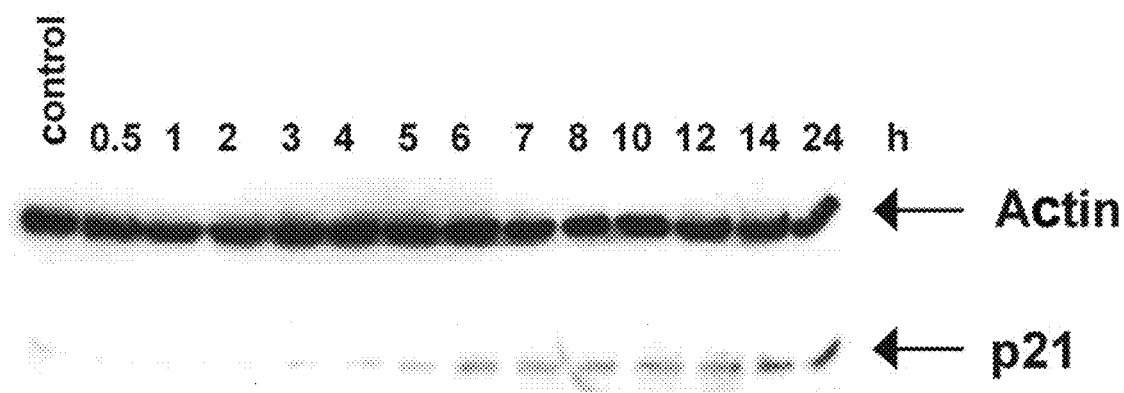
FIG. 6 shows $p21^{WAF-1}$ induction in MCF-7 cells 0.5-24 hours after the application of compound 28 in 1 µM concentration.
Figure 7:
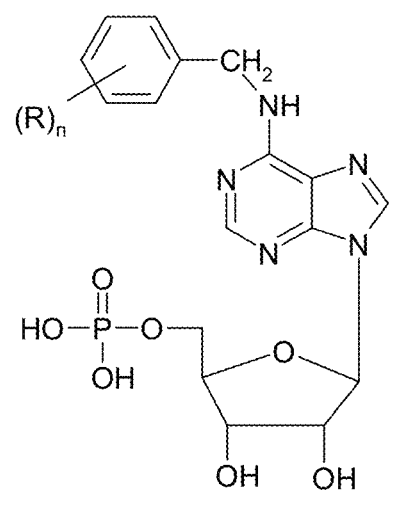

Induction of expression $p21^{WAF-1}$ natural cyclin-dependent kinases inhibitor by action of compound 28 in brest cancer cell line MCF-7-molecular mechanism of action $p21^{WAF-1}$ protein level changes in relation to compound 28 concentration MCF-7 cells cultured at 37° C. in 5% $CO_2$ atmosphere in DMEM medium supplemented with 10% foetal calf serum were treated with compound 28 concentration ranges of 0-100 µM. Compound 28 was added into the medium from the 100 mM stock solution in DMSO. Cells were harvested 12 hours after incubation with compound 28, centrifuged (1000 rpm, 4° C., 5 min), washed twice by ice-cold PBS and re-centrifuged. These washed cells were then lysed by 1×CSB (loading buffer for SDS-PAGE, i.e. electrophoresis of proteins in polyacrylamide gel containing SDS). Cell lysate proteins were separated by SDS-PAGE and transferred onto a nitrocelulose (NC) membrane. NC membrane was blocked by 5% skimmed milk, 0.1% Tween 20 in PBS. Protein level of $p21^{WAF-1}$ and actin (as a loaded protein volume control) were detected immunochemically using commercially available specific monoclonal antibodies anti-$p21^{WAF-1}$ (Ab-1, Calbiochem) and anti-Actin (Clone AC-40, Sigma-Aldrich). The primary antibodies bind to target proteins were detected using rabbit secondary peroxidase-labeled antibody (RAM-Px, DAKO), followed by chemiluminiscence (ECL, Amersham-Pharmacia). The efficient $p21^{WAF-1}$ protein induction is achieved in MCF-7 cells by treating these cells with compound 28 in the concentration range of units imol per liter of culture medium (FIG. 5).
$p21^{WAF}$-1 protein level changes in relation to compound 28 incubation period MCF-7 cells were incubated in the presence of 1 µmol of compound 28. In various time intervals from the moment of administration of 28 the cells were harvested and lyzed.

Subsequent SDS-PAGE and immunodetection allowed to determine changes in the $p21^{wAF}$-1 protein level depending on the incubation time in the presence of 28. Cell culture, harvesting, lysis and $p21^{wAF}$ protein and actin detection in lysates was performed in the same way as in point 1. An effective induction of $p21^{WAF-1}$ in the MCF-7 cells occurs within 6-24 hours after addition of 28 in 1 µmol concentration (FIG. 5).

Example 8

Immunosuppressive Activity

One of the most important parameters of specific cellular immunity is the proliferative response of lymphocytes to antigens or polyclonal mitogens. The majority of normal mammalian peripheral lymphocytes comprise resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). Compounds with ability to selectively inhibit lymphocyte proliferation are potent immunosuppressants. Variety of in vitro assays was developed to measure proliferative response of lymphocytes. The most commonly used is $^3$H-thymidine incorporation method.

During cell proliferation, DNA has to be replicated before the cell is divided into two daughter cells. This close association between cell doublings and DNA synthesis is very attractive for assessing cell proliferation. If labelled DNA precursors are added to the cell culture, cells that are about to divide incorporate the labelled nucleotide into their DNA. Traditionally, those assays usually involve the use of radiolabelled nucleosides, particularly tritiated thymidine ([$^3$H]-TdR). The amount of [$^3$H]-TdR incorporated into the cellular DNA is quantified by liquid scintillation counting.

Human heparinized peripheral blood was obtained from healthy volunteers by cubital vein punction. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 µg/ml streptomycin, 10% fetal calf serum and sodium bicarbonate).

The cells were diluted at target density of 1.100.000 cells/ml and were added by pipette (180 µl) into 96-well microtiter plates. Four-fold dilutions of the intended test concentration were added at time zero in 20 µl aliquots to the microtiter plate wells. Usually, test compound was evaluated at six 4-fold dilutions. In routine testing, the highest well concentration was 266.7 µM. All drug concentrations were examined in duplicates. All wells with exception of unstimulated controls were activated with 50 µl of concanavalin A (25 µg/ml). Incubations of cells with test compounds lasted for 72 hours at 37° C., in 5% $CO_2$ atmosphere and 100% humidity. At the end of incubation period, the cells were assayed by using the [$^3$H]-TdR:

Cell cultures were incubated with 0.5 µCi (20 µl of stock solution 500 µCi/ml) per well for 6 hours at 37° C. and 5% $CO_2$. The automated cell harvester was used to lyse cells in water and adsorb the DNA onto glass-fiber filters in the format of microtiter plate. The DNA incorporated [$^3$H]-TdR was retained on the filter while unincorporated material passes through. The filters were dried at room temperature overnight, sealed into a sample bag with 10-12 ml of scintillant. The amount of [$^3$H]-TdR present in each filter (in cpm) was determined by scintillation counting in a Betaplate liquid scintillation counter. The effective dose of immunosuppressant (ED) was calculated using the following equation: ED= ($CCPM_{drug\ exposed\ well}$/mean $CCPM_{control\ wells}$)×100%. The $ED_{50}$ value, the drug concentration inhibiting proliferation of 50% of lymphocytes, was calculated from the obtained dose response curves.

To evaluate immunosuppressive activity of substituted adenines, their ability to inhibit polyclonal mitogen induced proliferation of normal human lymphocytes was analyzed (Table 4). Our data demonstrate that these compounds have only marginal activity on $^3$H-thymidine incorporation in non-activated lymphocytes, nonetheless, they efficiently inhibit proliferation of activated lymphocytes. Effective immunosuppressive dose of new derivatives under in vitro conditions was close to 10-40 μM.

TABLE 4

Immunosupressive activity of novel derivatives

| SUBSTITUENT AT 6-POSITION OF PURINE | Human lymphocytes $ED_{50}$ (μM) |
|---|---|
| 2-hydroxybenzylamino | 6.7 |
| 3-hydroxybenzylamino | 12.8 |
| 2-fluorobenzylamino | 6.3 |
| 3-fluorobenzylamino | 11.5 |
| 4-fluorobenzylamino | 13.4 |
| 2-methylbenzylamino | 7.3 |
| 3-methylbenzylamino | 7.5 |
| 3,4-dihydroxybenzylamino | 9.4 |
| 2-hydroxy-3-chlorobenzylamino | 3.2 |
| 2-hydroxy-3-methoxybenzylamino | 1.2 |
| 2-hydroxy-4-methoxybenzylamino | 2.1 |
| 2-chlorobenzylamino | 8.7 |
| 3-chlorobenzylamino | 3.2 |
| 4-chlorobenzylamino | 3.3 |

Example 9

The Effect of Novel Compounds on Plant Cell Division

Cytokinin effect of newly prepared derivatives was tested using cytokinin-dependent tobacco callus. The cytokinin-dependent tobacco callus Nicotiana tabacum L. cv. Wisconsin 38 was maintained at 25° C. in darkness on modified MS medium, containing per 1 liter: 4 μmol of nicotinic acid, 2.4 μmol of pyridoxine hydrochloride, 1.2 μmol of thiamine, 26.6 μmol of glycine, 1.37 μmol of glutamine, 1.8 μmol of myo-inositol, 30 g of sucrose, 8 g of agar, 5.37 μmol of NAA and 0.5 μmol of the compound tested. Subcultivation was carried out every three weeks. Fourteen days before the bioassay, the callus tissue was transferred to the media without 6-benzylaminopurine. The biological activity was determined from the increase of the fresh callus weight after four weeks of cultivation. Five replicates were prepared for each concentration of the compound tested and the entire test was repeated twice. Kinetin (K), which is known to be highly active cytokinin, was used in each experiment as a control. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used. The stimulatory activity was calculated from the dose-dependent fresh weight callus growth curves.

From the obtained data, the concentration with the highest activity was selected for each compound tested. Relative activity of the compound at this concentration was calculated (Table 5). The activity obtained for $10^{-6}$ M of K was postulated as 100% of biological activity.

TABLE 5

The effect of Novel Substitution Derivatives of $N^6$-benzyladenosine-5'-monophosphate on the Growth of Cytokinin-Dependent Tobacco Callus Nicotiana tabacum L. cv. Wisconsins 38

| $N^6$-Substituent | Concentration with highest activity (mol · l$^{-1}$) | Activity (%) [$10^{-5}$ mol · l$^{-1}$ KR = 100%] |
|---|---|---|
| 2-fluorobenzylamino | $10^{-6}$ | 100 ± 9 |
| 3-fluorobenzylamino | $10^{-5}$ | 103 ± 6 |
| 2-chlorobenzylamino | $10^{-6}$ | 121 ± 4 |
| 3-chlorobenzylamino | $10^{-5}$ | 109 ± 5 |
| 2-bromobenzylamino | $10^{-5}$ | 100 ± 4 |
| 3-bromobenzylamino | $10^{-6}$ | 102 ± 11 |
| 2-methylbenzylamino | $10^{-6}$ | 108 ± 4 |
| 2-methoxylbenzylamino | $10^{-5}$ | 108 ± 1 |
| 3-methoxylbenzylamino | $10^{-6}$ | 102 ± 1 |
| 3-chloro-4-fluorobenzylamino | $10^{-6}$ | 107 ± 4 |
| 2-chloro-4-fluorobenzylamino | $10^{-5}$ | 108 ± 4 |
| 3,5-difluorobenzylamino | $10^{-6}$ | 105 ± 3 |
| 2,4,5-trifluorobenzylamino | $10^{-5}$ | 105 ± 3 |

Example 10

Dry Capsules 5000 capsules, each of which contains 0.25 g of a compound of the formula I as an active ingredient, are prepared as follows:
Composition

| Active ingredient | 1250 g |
|---|---|
| Talc | 180 g |
| Wheat starch | 120 g |
| Magnesium stearate | 80 g |
| Lactose | 20 g |

Preparation process: The powdered substances mentioned are pressed through a sieve of mesh width 0.6 mm. Portions of 0.33 g of the mixture are transferred to gelatine capsules with the aid of a capsule-filling machine.

Example 11

Soft Capsules 5000 soft gelatine capsules, each of which contains 0.05 g of a compound of the formula I as an active ingredient, are prepared as follows:
Composition

| Active ingredient | 250 g |
|---|---|
| Lauroglycol | 2 liters |

Preparation process: The powdered active ingredient is suspended in Lauroglykol® (propylene glycol laurate, Gattefossé S. A., Saint Priest, France) and ground in a wet-pulveriser to a particle size of about 1 to 3 mm. Portions of in each case 0.419 g of the mixture are then transferred to soft gelatine capsules by means of a capsule-filling machine.

Example 12

Soft Capsules 5000 soft gelatine capsules, each of which contains 0.05 g of a compound of the formula I as an active ingredient, are prepared as follows:

Composition

| Active ingredient | 250 g |
| --- | --- |
| PEG 400 | 1 liter |
| Tween 80 | 1 liter |

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Ind., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:
1. Compounds according to formula I,

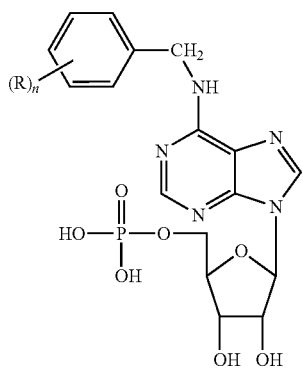

I

Wherein
(R)$_n$ represents 1 to 4 substituents R, which can be the same or different,
and R is selected from the group comprising C1 to C8 alkyl, C1 to C8 alkoxy, halogen, hydroxy, and mercapto groups, and wherein when at least one substituent R is hydroxy, a hydroxy group is in position 2 of the phenyl ring;
and their pharmaceutically acceptable salts.

2. Compounds of formula I according to claim 1, wherein the compounds are selected from the group containing 6-(2-fluorobenzylamino)purine riboside-5"-monophosphate, 6-(3-fluorobenzylamino)purine riboside-5"-monophosphate, 6-(4-fluorobenzylamino)purine riboside-5"-monophosphate, 6-(2-bromobenzylamino)purine riboside-5"-monophosphate, 6-(3-bromoobenzylamino)purine riboside-5"-monophosphate, 6-(4-bromobenzylamino)purine riboside-5"-monophosphate, 6-(2-iodobenzylamino)purine riboside-5"-monophosphate, 6-(3-iodobenzylamino)purine riboside-5"-monophosphate, 6-(4-iodobenzylamino)purine riboside-5"-monophosphate, 6-(2-chlorobenzylamino)purine riboside-5"-monophosphate, 6-(3-chlorobenzylamino)purine riboside-5"-monophosphate, 6-(4-chlorobenzylamino)purine riboside-5"-monophosphate, 6-(2-methylbenzylamino) purine riboside-5"-monophosphate, 6-(3-methylbenzylamino)purine riboside-5"-monophosphate, 6-(4-methylbenzylamino)purine riboside-5"-monophosphate, 6-(2-methoxybenzylamino)purine riboside-5"-monophosphate, 6-(3-methoxybenzylamino)purine riboside-5"-monophosphate, 6-(4-methoxybenzylamino)purine riboside-5"-monophosphate, 6-(2-hydroxybenzylamino)purine riboside-5"-monophosphate, 6-(2-ethoxybenzylamino)purine riboside-5"-monophosphate, 6-(3-ethoxybenzylamino)purine riboside-5"-monophosphate, 6-(4-ethoxybenzylamino)purine riboside-5"-monophosphate, 6-(4-ethylbenzylamino)purine riboside-5"-monophosphate, 6-(4-pentylbenzylamino)purine riboside-5"-monophosphate, 6-(4-pentyloxybenzylamino)purine riboside-5"-monophosphate, 6-(4-octylbenzylamino)purine riboside-5"-monophosphate, 6-(3,5-dibromobenzylamino)purine riboside-5"-monophosphate, 6-(3,5-dibromo-4-methoxybenzylamino)purine riboside-5"-monophosphate, 6-(2,3-dichlorobenzylamino)purine riboside-5"-monophosphate, 6-(2,4-dichlorobenzylamino)purine ribose de-5"-monophosphate, 6-(2,5-dichlorobenzylamino)purine ribose de-5"-monophosphate, 6-(2,6-ichlorobenzylamino)purine riboside-5"-monophosphate, 6-(3,4-dichlorobenzylamino)purine riboside-5"-monophosphate, 6-(3,5-dichlorobenzylamino)purine riboside-5"-monophosphate, 6-(2,3,4,5-tetrafluorobenzylamino)purine riboside-5"-monophosphate, 6-(2-chloro-3,6-difluorobenzylamino)purine riboside-5"-monophosphate, 6-(5-chloro-2-fluorobenzylamino)purine riboside-5"-monophosphate, 6-(2,3,4-trifluorobenzylamino)purine riboside-5"-monophosphate, 6-(2,3,5-trifluorobenzylamino)purine riboside-5"-monophosphate, 6-(2,4,5-trifluorobenzylamino)purine riboside-5"-monophosphate, 6-(3,4,5-trifluorobenzylamino)purine riboside-5"-monophosphate, 6-(2,3,6-trifluorobenzylamino)purine riboside-5"-monophosphate, 6-(3-chloro-2,6-difluorobenzylamino)purine riboside-5"-monophosphate, 6-(2-chloro-6-fluorobenzylamino)purine riboside-5"-monophosphate, 6-(2,6-difluorobenzylamino)purine riboside-5"-monophosphate, 6-(2,4-difluorobenzylamino)purine riboside-5"-monophosphate, 6-(3,4-difluorobenzylamino)purine riboside-5"-monophosphate, 6-(2,5-difluorobenzylamino)purine riboside-5"-monophosphate, 6-(3,5-difluorobenzylamino)purine riboside-5"-monophosphate, 6-(2-chloro-6-fluoro-3-methylbenzylamino)purine riboside-5"-monophosphate, 6-(6-chloro-2-fluoro-3-methylbenzylamino)purine riboside-5"-monophosphate, 6-(2,3-difluoro-4-methylbenzylamino)purine riboside-5"-monophosphate, 6-(2,6-difluoro-3-methylbenzylamino)purine riboside-5"-monophosphate, 6-(3-chloro-2,6-difluorobenzylamino)purine riboside-5"-monophosphate, 6-(3-fluoro-4-methylbenzylamino)purine riboside-5"-monophosphate, 6-(4-fluoro-3-methylbenzylamino)purine riboside-5"-monophosphate, 6-(5-fluoro-2-methylbenzylamino)purine riboside-5"-monophosphate, 6-(2-chloro-3,6-difluorobenzylamino)purine riboside-5"-monophosphate, 6-(2-chloro-4-fluorobenzylamino)purine riboside-5"-monophosphate, 6-(2,4-dihydroxybenzylamino)purine riboside-5"-monophosphate, 6-(2,5-dihydroxybenzylamino)purine riboside-5"-monophosphate, 6-(2,6-dihydroxybenzylamino)purine riboside-5"-monophosphate, 6-(3,4-dimethoxybenzylamino)purine riboside-5"-monophosphate, 6-(3,5-dimethoxybenzylamino)purine riboside-5"-monophosphate, 6-(2,3-dimethoxybenzylamino)purine riboside-5"-monophosphate, 6-(2,4-dimethoxybenzylamino)purine riboside-5"-monophosphate, 6-(2,5-dimethoxybenzylamino)purine riboside-5"-monophosphate, 6-(2,6-dimethoxybenzylamino)purine riboside-5"-monophosphate, 6-(2-hydroxy-3-methoxybenzylamino)purine riboside-5"-monophosphate, 6-(2-hydroxy-4-methoxybenzylamino)purine riboside-5"-monophosphate, 6-(2-hydroxy-5-methoxybenzylamino)purine riboside-5"-monophosphate, 6-(2-hydroxy-6-methoxybenzylamino)purine riboside-5"-monophosphate, 6-(2-hydroxy-3,4-dimethoxybenzylamino)purine riboside-5"-monophosphate, 6-(2-hydroxy-3,5-dimethoxybenzylamino)

purine riboside-5"-monophosphate, 6-(2-hydroxy-3,6-dimethoxybenzylamino)purine riboside-5"-monophosphate, 6-(2-hydroxy-4,5-dimethoxybenzylamino)purine riboside-5"-monophosphate, 6-(2-hydroxy-4,6-dimethoxybenzylamino)purine riboside-5"-monophosphate, 6-(2-hydroxy-5,6-dimethoxybenzylamino)purine riboside-5"-monophosphate, 6 (2,3-dihydroxy-4-methoxybenzylamino)purine riboside-5"-monophosphate, 6-(2,3-dihydroxy-5-methoxybenzylamino)purine riboside-5"-monophosphate, 6-(2,3-dihydroxy-6-methoxybenzylamino)purine riboside-5"-monophosphate, 6-(2,4-dihydroxy-3-methoxybenzylamino)purine riboside-5"-monophosphate, 6-(2,4-dihydroxy-5-methoxybenzylamino)purine riboside-5"monophosphate, 6-(2,4-dihydroxy-6-methoxybenzylamino)purine riboside-5"-monophosphate, 6-(2,5-dihydroxy-3-methoxybenzylamino)purine riboside-5"-monophosphate, 6-(2,5-dihydroxy-4-methoxybenzylamino)purine riboside-5"-monophosphate, 6-(2,5-dihydroxy-6-methoxybenzylamino)purine riboside-5"-monophosphate, 6-(2,6-dihydroxy-3-methoxybenzylamino)purine riboside-5"-monophosphate, 6-(2,6-dihydroxy-4-methoxybenzylamino)purine riboside-5"-monophosphate, 6-(2,6-dihydroxy-5-methoxybenzylamino)purine riboside-5"-monophosphate, 6-(3,4-dihydroxy-2-methoxybenzylamino)purine riboside-5"-monophosphate, 6-(3,4-dihydroxy-5-methoxybenzylamino)purine riboside-5"-monophosphate, 6-(3,4-dihydroxy-6-methoxybenzylamino)purine riboside-5"-monophosphate, 6-(3,5-dihydroxy-2-methoxybenzylamino)purine riboside-5"-monophosphate, 6-(3,5-dihydroxy-4-methoxybenzylamino)purine riboside-5"-monophosphate, 6-(3,5-dihydroxy-6-methoxybenzylamino)purine riboside-5"-monophosphate, 6-(2,3,4-trimethoxybenzylamino)purine riboside-5"-monophosphate, 6-(2,4,5-trimethoxybenzylamino)purine riboside-5"-monophosphate, 6-(2,4,6-trimethoxybenzylamino)purine riboside-5"-monophosphate, 6-(3,4,5-trimethoxybenzylamino)purine riboside-5"-monophosphate, 6-(2-hydroxy-3,4,5-trimethoxybenzylamino)purine riboside-5"-monophosphate, 6-(2-hydroxy-3,4,6-trimethoxybenzylamino)purine riboside-5"-monophosphate, 6-(2-hydroxy-4,5,6-trimethoxybenzylamino)purine riboside-5"-monophosphate, 6-(2,4,6-trimethoxybenzylamino)purine riboside-5"-monophosphate, 6-(2,3,4-trihydroxybenzylamino)purine riboside-5"-monophosphate, 6-(2,4,6-trihydroxybenzylamino)purine riboside-5"-monophosphate, 6-(2,3,4-trihydroxybenzylamino)purine riboside-5"-monophosphate, 6-(2-hydroxy-3-chlorobenzylamino)purine riboside-5"-monophosphate, 6-(2-hydroxy-4-chlorobenzylamino)purine riboside-5"-monophosphate, 6-(2-hydroxy-5-chlorobenzylamino)purine riboside-5"-monophosphate, 6-(2-hydroxy-6-chlorobenzylamino)purine riboside-5"-monophosphate, 6-(2-hydroxy-3-iodobenzylamino)purine riboside-5"-monophosphate, 6-(2-hydroxy-4-iodobenzylamino)purine riboside-5"-monophosphate, 6-(2-hydroxy-5-iodobenzylamino)purine riboside-5"-monophosphate, 6-(2-hydroxy-6-iodobenzylamino)purine riboside-5"-monophosphate, 6-(2-hydroxy-3-bromobenzylamino)purine riboside-5"-monophosphate, 6-(2-hydroxy-4-bromobenzylamino)purine riboside-5"-monophosphate, 6-(2-hydroxy-5-bromobenzylamino)purine riboside-5"-monophosphate, 6-(2-hydroxy-6-bromobenzylamino)purine riboside-5"-monophosphate, 6-(2-hydroxy-3-fluorobenzylamino)purine riboside-5"-monophosphate, 6-(2-hydroxy-4-fluorobenzylamino)purine riboside-5"-monophosphate, 6-(2-hydroxy-5-fluorobenzylamino)purine riboside-5"-monophosphate, 6-(2-hydroxy-6-fluorobenzylamino)purine riboside-5"-monophosphate, 6-(2-hydroxy-3-methylbenzylamino)purine riboside-5"-monophosphate, 6-(2-hydroxy-4-methylbenzylamino)purine riboside-5"-monophosphate, 6-(2-hydroxy-5-methylbenzylamino)purine riboside-5"-monophosphate, 6-(2-hydroxy-6-methylbenzylamino)purine riboside-5"-monophosphate, 6-(2,3-dihydroxy-4-chlorobenzylamino)purine riboside-5"-monophosphate, 6-(2,3-d-hydroxy-5-chlorobenzylamino)purine riboside-5"-monophosphate, 6-(2,5-dihydroxy-4-chlorobenzylamino)purine riboside-5"-monophosphate, 6-(2,6-dihydroxy-4-chlorobenzylamino)purine riboside-5"-monophosphate, 6-(2,6-dihydroxy-4-iodobenzylamino)purine riboside-5"-monophosphate, 6-(2,6-dihydroxy-3-chlorobenzylamino)purine riboside-5"-monophosphate, 6-(2,6-dihydroxy-3-bromobenzylamino)purine riboside-5"-monophosphate, 6-(2,6-dihydroxy-3-iodobenzylamino)purine riboside-5"-monophosphate, 6-(2,6-dihydroxy-3-fluoroobenzylamino)purine riboside-5"-monophosphate, 6-(2,6-dihydroxy-3,5-dichlorobenzylamino)purine riboside-5"-monophosphate, 6-(2,6-dihydroxy-3,5-dibromobenzylamino)purine riboside-5"-monophosphate, 6-(2,6-dihydroxy-3,5-diiodobenzylamino)purine riboside-5"-monophosphate, 6-(2,6-dihydroxy-3,5-difluorobenzylamino)purine riboside-5"-monophosphate, 6-(3,4-dimethylbenzylamino)purine riboside-5"-monophosphate, 6-(2,3-dimethylbenzylamino)purine riboside-5"-monophosphate, 6-(2,4-dimethylbenzylamino)purine riboside-5'-monophosphate, 6-(2,6-dimethylbenzylamino)purine riboside-5'-monophosphate, 6-(3-fluoro-4-methylbenzylamino)purine riboside-5"-monophosphate, 6-(2-chloro-3,4-dimethoxybenzylamino)purine riboside-5"-monophosphate, 6-(2-chloro-4-fluorobenzylamino)purine riboside-5"-monophosphate, 6-(3-chloro-4-fluorobenzylamino)purine riboside-5"-monophosphate, 6-(2-chloro-6-methylbenzylamino)purine riboside-5"-monophosphate, 6-(3-chloro-2-methylbenzylamino)purine riboside-5"-monophosphate, 6-(3-chloro-4-methylbenzylamino)purine riboside-5"-monophosphate, 6-(5-chloro-2-methoxybenzylamino)purine riboside-5"-monophosphate, 6-(2-chloro-4-fluorobenzylamino)purine riboside-5"-monophosphate, 6-(3-bromo-4-methoxybenzylamino)purine, 6-(4-butoxybenzylamino)purine riboside-5"-monophosphate, 6-(4-butoxybenzylamino)purine riboside-5"-monophosphate, 6-(4-t-butylbenzylamino)purine riboside-5"-monophosphate, 6-(4-t-butyl-2,6-dimethylbenzylamino)purine riboside-5"-monophosphate, 6-(2,4,5-trichlorobenzylamino)purine riboside-5"-monophosphate, 6-(2,4,5-trichlorobenzylamino)purine riboside-5"-monophosphate, 6-(2,4,6-trichlorobenzylamino)purine riboside-5"-monophosphate, 6-(2,3,4-trichlorobenzylamino)purine riboside-5"-monophosphate, 6-(2,3,5-trichlorobenzylamino)purine riboside-5"-monophosphate, 6-(2,3,6-trichlorobenzylamino)purine riboside-5"-monophosphate, 6-(2,5,6-trichlorobenzylamino)purine riboside-5"-monophosphate.

3. A method of preparation of a compound of formula 1 according to claim 1, the method comprising a nucleophilic substitution of 6-halogenopurine riboside-5"-monophosphate, wherein halogen is selected from the group containing bromine, chlorine or fluorine, with benzylamine substituted by one to four substituents R, which can be the same or different.

4. Compounds of formula I according to claim 1 for use as medicaments.

5. Compounds of formula I according to claim 1 for use as proteinkinase inhibitors.

6. Compounds of formula I according to claim 1 for use for treating disorders involving aberrant cell proliferation and/or aberrant cell death.

7. Compounds of formula I according to claim 1 for use in the treatment of a disorder selected from the group comprising cancer, leukemia, restenosis, rheumatoid arthritis, lupus, type I diabetes, multiple sclerosis, Alzheimer's disease, parasitoses caused by animals, fungi and protists, polycystic kidney disease, graft rejection, graft versus host disease, and gout.

8. A method of treating disorders which involve at least one of aberrant cell proliferation and aberrant cell death, the method comprising administering one or more compounds of formula I according to claim 1.

9. A method of at least one of suppressing immunostimulation and suppressing transplant rejection, the method comprising administering one or more compounds of formula I according to claim 1.

10. A method of at least one of suppressing immunostimulation and suppressing transplant rejection, the method comprising administering one or more compounds of formula I according to claim 2.

11. A method of regulating at least one of tissue proliferation and tissue morphogenesis, the method comprising administering one or more compounds of formula I according to claim 1 to tissue in tissue culture.

12. At least one compound of formula I according to claim 1, wherein the compound of formula I is part of at least one of: an affinity absorption matrix, immobilized enzyme for process control, immunoassay reagent, a compound labeled by 14C, 3H, avidin or biotin, and an oligonucleotide labeled by 14C, 3H, avidin or biotin.

13. A method of cloning at least one of plant cells and mammalian cells, the method comprising administering at least one compound of formula I according to claim 1 to cells being grown in vitro.

14. A method of regulating growth of at least one of a plant, a microorganism, a yeast, a fungi, and an animal, the method comprising administering at least on compound of formula I according to claim 1.

15. A therapeutic composition.

16. A method of regulating growth of non-human mammal cells, the method comprising administering at least on compound of formula I according to claim 1.

17. A method of treating disorders which involve at least one of aberrant cell proliferation and aberrant cell death, the method comprising administering one or more compounds of formula Ia to a warm-blooded animal:

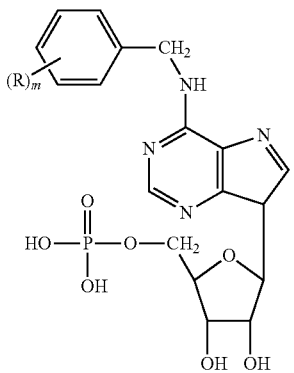

Ia wherein $(R)_n$ represents 1 to 4 substituents R, which can be the same or different, and R is selected from the group comprising C1 to C8 alkyl, C1 to C8 alkoxy, halogen, hydroxy, and mercapto groups, and their pharmaceutically acceptable salts.

18. A method of treating disorders according to claim 17, the method comprising administering one or more compounds of formula Ia according to claim 17, wherein said one or more compounds of formula is are administered to treat a disorder selected from the group comprising cancer, leukemia, restenosis, rheumatoid arthritis, lupus, type I diabetes, multiple sclerosis, Alzheimer's disease, parasitoses caused by animals, fungi and protists, polycystic kidney disease, graft rejection, graft versus host disease, and gout.

* * * * *